(12) United States Patent
Kirk et al.

(10) Patent No.: US 11,458,327 B2
(45) Date of Patent: Oct. 4, 2022

(54) HIGH-POWER PULSED ELECTROMAGNETIC FIELD APPLICATOR SYSTEM

(71) Applicant: REGENESIS BIOMEDICAL, INC., Scottsdale, AZ (US)

(72) Inventors: Martin Kirk, Scottsdale, AZ (US); Shanil Merchant, Phoenix, AZ (US); Joseph Bright, Phoenix, AZ (US); Randy Chavez, Mesa, AZ (US); Scott Brooks, Phoenix, AZ (US); Scott Cowling, Tempe, AZ (US); Frank Contreras, Phoenix, AZ (US); Charles Mesarosh, Mesa, AZ (US)

(73) Assignee: Regenesis Biomedical, Inc., Scottsdale, AZ (US)

( * ) Notice: Subject to any disclaimer, the term of this patent is extended or adjusted under 35 U.S.C. 154(b) by 242 days.

(21) Appl. No.: 16/633,734

(22) PCT Filed: Jul. 24, 2018

(86) PCT No.: PCT/US2018/043538
§ 371 (c)(1),
(2) Date: Jan. 24, 2020

(87) PCT Pub. No.: WO2019/023265
PCT Pub. Date: Jan. 31, 2019

(65) Prior Publication Data
US 2020/0206523 A1 Jul. 2, 2020

Related U.S. Application Data

(60) Provisional application No. 62/536,409, filed on Jul. 24, 2017.

(51) Int. Cl.
*A61N 2/02* (2006.01)
*A61N 1/02* (2006.01)
(Continued)

(52) U.S. Cl.
CPC ............. *A61N 2/02* (2013.01); *A61N 1/025* (2013.01); *A61N 1/0468* (2013.01); *A61N 1/40* (2013.01); *A61N 2/004* (2013.01)

(58) Field of Classification Search
CPC ........ A61N 2/02; A61N 1/025; A61N 1/0468; A61N 1/40; A61N 2/004; A61N 1/0456; A61N 1/0452; A61N 1/36014
(Continued)

(56) References Cited

U.S. PATENT DOCUMENTS 4,926,881 A * 5/1990 Ichinomiya ............... A61N 1/06
607/155
5,314,401 A 5/1994 Tepper
(Continued)

FOREIGN PATENT DOCUMENTS

| WO | WO2012/048302 A2 | 4/2012 |
| WO | WO2013/023265 A1 | 1/2019 |
| WO | WO2019/183622 A1 | 9/2019 |

OTHER PUBLICATIONS

Akan et al.; Extremely low-frequency electromagnetic fields affect the immune response of monocyte-derived macrophages to pathogens; Bioelectromagnetics; 31(8); pp. 683-612; Dec. 2010.
(Continued)

*Primary Examiner* — Sunita Reddy
(74) *Attorney, Agent, or Firm* — Shay Glenn LLP

(57) ABSTRACT

Described herein are high-power pulsed electromagnetic field (PEMF) applicator systems. The systems can comprise a base housing including a controller configured to generate a low-power control signal and one or more applicators coupled to the base. Each applicator can include a drive circuitry comprising a generator configured to receive the low-power control signal and to produce, in the applicator, a high-power, pulsed electromagnetic field signal based on the low-power control signal. The high-power pulsed elec-
(Continued)

tromagnetic field signal can have a power of greater than 40W. Each applicator can further include a coil circuit configured to emit the high-power pulsed electromagnetic field signal, and an electromagnetic energy shield disposed between the drive circuitry and the coil circuit.

18 Claims, 17 Drawing Sheets

(51) Int. Cl.
*A61N 1/40* (2006.01)
*A61N 1/04* (2006.01)
*A61N 2/00* (2006.01)

(58) Field of Classification Search
USPC .................................................. 600/9–15
See application file for complete search history.

(56) References Cited

U.S. PATENT DOCUMENTS

| | | | |
|---|---|---|---|
| 6,162,166 A | 12/2000 | Neuwirth | |
| 6,174,276 B1 | 1/2001 | Blackwell | |
| 6,261,221 B1* | 7/2001 | Tepper | A61N 2/02 600/13 |
| 6,334,069 B1 | 12/2001 | George et al. | |
| 6,443,883 B1 | 9/2002 | Ostrow et al. | |
| 6,463,336 B1 | 10/2002 | Mawhinney | |
| 6,967,281 B2 | 11/2005 | George et al. | |
| 6,974,961 B1 | 12/2005 | George et al. | |
| 8,195,287 B2 | 6/2012 | Dacey et al. | |
| 10,245,439 B1 | 4/2019 | Schwarz et al. | |
| 10,441,807 B2 | 10/2019 | Moffett | |
| 2004/0176805 A1* | 9/2004 | Whelan | A61N 2/02 607/2 |
| 2004/0210254 A1 | 10/2004 | Burnett et al. | |
| 2005/0010163 A1 | 1/2005 | Aoki et al. | |
| 2005/0059153 A1 | 3/2005 | George et al. | |
| 2007/0060981 A1 | 3/2007 | Pilla et al. | |
| 2008/0004904 A1 | 1/2008 | Tran | |
| 2008/0249350 A1 | 10/2008 | Marchitto et al. | |
| 2009/0228071 A1 | 9/2009 | Bourget | |
| 2011/0065976 A1* | 3/2011 | Chornenky | A61N 1/40 600/14 |
| 2011/0112352 A1* | 5/2011 | Pilla | A61N 1/40 600/14 |
| 2011/0196365 A1 | 8/2011 | Kim et al. | |
| 2012/0302821 A1 | 11/2012 | Burnett | |
| 2013/0190599 A1 | 7/2013 | Wyeth et al. | |
| 2013/0245486 A1 | 9/2013 | Simon et al. | |
| 2014/0012108 A1 | 1/2014 | McPeak | |
| 2014/0148870 A1 | 5/2014 | Burnett | |
| 2014/0213844 A1 | 7/2014 | Pilla et al. | |
| 2014/0249355 A1 | 9/2014 | Martinez | |
| 2014/0265611 A1 | 9/2014 | Fern et al. | |
| 2014/0336443 A1 | 11/2014 | Maharaj | |
| 2015/0297910 A1 | 10/2015 | Dimino et al. | |
| 2016/0346561 A1 | 12/2016 | Ron Edoute et al. | |
| 2018/0043174 A1 | 2/2018 | Gurfein | |
| 2018/0071545 A1 | 3/2018 | Saitoh et al. | |
| 2018/0126185 A1 | 5/2018 | Hochstenbach | |
| 2018/0318598 A1 | 11/2018 | Russo | |
| 2019/0388676 A1 | 12/2019 | Babico | |
| 2020/0001101 A1 | 1/2020 | Moffett | |
| 2021/0023382 A1 | 1/2021 | Kirk et al. | |
| 2022/0118268 A1 | 4/2022 | Kirk et al. | |

OTHER PUBLICATIONS

Apfelbaum et al.; Postoperative pain experience: results from a national survey suggest postoperative pain continues to be undermanaged: Anesthesia and Analgesia; 97(2); pp. 534-540; Aug. 2003.

Baranano et al.; Biliverdin reductase: a major physiologic cytoprotectant; Proceedings of the National Academy of Sciences; 88(25); pp. 16093-16098; Dec. 10, 2002.

Basbaum et al.; Cellular and molecular mechanisms of pain: Cell; 139(2); pp. 267-284; Oct. 16, 2009.

Brennan et al.; Cytokine expression in chronic inflammatory disease; British Medical Bulletin; 51(2); pp. 368-384; Apr. 1995.

Buckley et al.; The resolution of inflammation; Nature Reviews Immunology; 13(1); pp. 59-66; Jan. 2013.

Catala; Five decades with polyunsaturated Fatty acids: chemical synthesis, enzymatic formation, lipid peroxidation and its biological effects; Journal of Lipids; http://dx.doi.org/10.1155/2013/710290; 20 pages; year of pub. suficienily earlier than effective US filing date and any foreign priority date) 2013.

Clark et al.; Neuropathic pain and cytokines: current perspectives; Journal of Pain Research; 6; pp. 803-814; doi: 10.2147/JPR. S53660; 12 pages; Nov. 21, 2013.

Commins et al.; The extended IL-10 superfamily: IL-10, IL-19, IL-20 IL-22, IL-24, IL-26, IL-28, and IL-29; Journal of Allergy and Clinical Immunology; 121(5); pp. 1108-1111; May 2008.

Dutra et al.; Heme on innate immunity and inflammation; Frontiers in Pharmacology; 5; Article 115; dol: 10.3389/fphar.2014.00115; 20 pages; May 2014.

Gou et al.; Meta-anaiysis of clinical efficacy of pulsed radio frequency energy treatment; Annals of Surgery; 255(3); pp. 457-467; Mar. 2012.

Greene et al.; Regulation of inflammation in cancer by eicosanoids; Prostaglandins and Other Lipid Mediators; 96(1-4); pp. 27-36; 28 pages; (Author Manuscript); Nov. 2011.

Guo et al.; Pulsed radio frequency energy (PRFE) use in human medical applications; Electromagnetic Biology and Medicine; 30(1); pp. 21-45; Mar. 2011.

Hasegawa et al.; Modifying TNF alpha for therapeutic use: a perpective on the TNF receptor system; Mini Reviews in Medicinal Chemistry; 1(1); pp. 5-16; May 2001.

Haworth et al.; Resolving the problem of persistence in the switch from acute to chronic inflammation; Proceedings of the National Academy of Sciences: 104(52); pp. 20647-20648; Dec. 26, 2007.

He et al.; Exposure to extremely low-frequency electremagnetic fields modulates Ns+ currents in rat cerebellar granule cells through increase of AA/PGE2 and EP receptor-mediated cAMP/PKA pathway, Plos One; 8(1); pp. e54376; 13 pages; Jan. 22, 2013.

Heden et al.: Effects of pulsed electromagnetic fields on postoperative pain: a double-blind randomized pilot study in breast augmeniation patients; Aesthetic Plastic Surgery; 32(4); pp. 660-666; Jul. 2008.

Ji et al; Emerging roles of resolvins in the resolution of inflammation and pain; Trenads in Neurosciences; 34(11); pp. 599-609; 20 pages; (Author Manuscript); Nov. 2011.

Kunkel et al.; Suppression of acute and chronic inflammation by orally administered prostaglandins; Arthritis and Rheumatism: Official Journal of the American College of Eheumatology 24(9); pp. 1151-1158; Sep. 1981.

Livak et al.; Analysis of relative gene expression data using real-time quantitative PCR and the 2-??CT method; Methods; 25(4); pp. 402-408; Dec. 2001.

Markov et al.; Interaction between electromagnetic fields and the immune system; possible mechanisms for pain control; Ayrapetyan SNM, M.S., ed.; Bioelectromagnetics Current Concepts; Dordrecht: Springer; pp. 213-225; (year of pub. sufficiently earlier than effective US filing date and any foreign priority date) 2006.

McIntyre el al.; Molecular mechanisms of early inflammation; Thromb Haemost; 78(I):302-305; Jul. 1997.

Medzhitov et al.; Transcriptional control of the inflammatory response; Nature Reviews Immunology; 9(10); pp. 692-703; Oct. 2009.

Medzhitov: Origin and physiological roles of inflammation; Nature; 454(7203); pp. 428-435; Jul. 23, 2008.

Medzhitov; Inflammation 2010: new adventures of an old flame; Cell; 140(6); pp. 771-776; Mar. 19, 2010.

Moffett et al.; Activation of endogenous opioid gene expression in human keratinocytes and fibrobtasts by pulsed radiofrequency energy fields; Journal of Pain Research; 5; pp. 347-357: Sep. 19, 2012.

(56) References Cited

OTHER PUBLICATIONS

Moffett et al ; Pulsed radio frequency energy field treatment of cells in culture results in increased expression of genes involved in angiogenesis and tissue remodeling during wound healing; The Journal of Diabetic Foot Complications; 3(2); pp. 30-39; (year of pub. sufficiently earlier than effective US filing date and any foreign priority date) 2011.

Moffet et al.: Pulsed radio frequency energy field treatment of cells in culture results in increased expression of genes involved in inflammation phase of tower extremity diabetic wound healing; The Journal of Diabetic Foot Complications; 2(3); pp. 57-64; (year of pub. sufficiently earlier than effective US filing date and any foreign priority date) 2010.

Moreland; Inhibitors of tumor necrosis factor for rheumatoid arthritis; 66(6); pp. 367-374; Jun. 1999.

Moreland; Inhibitors of tumor necrosis factor for rheumatoid arthritis; The Journal of Rheumatology; 57; pp. 7-15; May 1, 1999.

Mosser et al.; Interleukin-10: new perspectives on an old cytokine; Immunological Reviews; 226(1); pp. 205-218; 22 pages; (Author Manuscript); Dec. 2008.

Nathan; Nonresolving inflammation; Cell; 140(6); pp. 871-882; Mar. 19, 2010.

Neher et al.; Molecular mechanisms of inflammation and tissue injury after major trauma 'is complement the "bad guy"? Journal of Biomedical Sciences; 18(1); pp. 90; doi: 10.1186/1423/1423-0127-18-90; Dec. 2011.

Novo et al.; Redox mechanisms in hepatic chronic wound healing and fibrogenesis; Fibrogenesis and tissue repair; 1(1); doi:10.1186/1755-1536-1-5; 58 pages; Dec. 2008.

Pelletier et al., New tricks from an old dog: rnitochondria) redox signaling in cellular inflammation; InSeminars in Immunology; 24(6); pp. 384-392, 21 pages; (Author Manuscript); Dec. 2012.

Pilla et al.; EMF signals and ion/ligand binding kinetics: prediction of bioeffective waveform parameters; Bioelectrochemisrty and Bioenergetics; 48(1); pp. 27-34; Feb. 1999.

Pilla et al.; Nonthermal electromagnetic fields: from first messenger to therapeutic applications; Electromagnetic Biology and Medicine; 32(2); pp. 123-136; Jun. 2013.

Pons et al.; Pro-inflammatory and anti-inflammatory effects of the stable prostaglandin D2 analogue; European Journal of Pharmacology; 261(3); pp. 237-247; Aug. 22, 1994.

Rohde et al.; Effects of pulsed electromagnetic fileds on interleukin-1 beta and postoperative pain: a double-blind, placebo-controlled, pilot study in breast reduction patients; Plastic and Reconstructive Surgery; 125(6); pp. 1620-1629; Jun. 2010.

Ross et al.; Effect of time-varied magnetic field on inflammatory response in macrophage cell line RAW 264.7; Electromagnetic Biology and Medicine; 32(1); pp. 59-69; Mar. 2013.

Ross et al.: Effect of pulsed electromagnetic field on inflammatory pathway markers in RAW 264.7 murine macrophages; Journal of inflammation Research; 6; pp. 45-51; (year of pub. sufficiently earlier than effective US filing date and any foreign priority date) 2013.

Selvam et al.; Low frequency and few intensity pulsed electromagnetic field exerts its antinflammatory effect through restoration of plasma membrane calcium; Life Spences; 80(26); pp. 2403-2410; Jun. 6, 2007.

Serhan et al.; Anti-inflammatory and proresolving lipid mediators; Annu. Rev. Pathmechdis. Mech. Dis.; 3; pp. 279-312; 43 pages: (Author Manuscript); Feb. 28, 2008.

Serhan et al.; Maresins: novel macrophage mediators with potent anti-inflammatory and proresolving actions; Journal of Experimental Medicine; 206(1); pp. 15-23; Jan. 16, 2009.

Serhan et al ; Protectins and maresins: New pro-resolvng familes of mediators in acute inflammation and resolution bioactive metabolome; Biochimica et Bipphysics Acta (BBA)—Molecular and Cell Biology of Lipid; 1851(4), pp. 397-413; 40 pages; (Author Manuscpt); Apr. 30, 2015.

Serhan; Novel lipid mediators and resolution mechanisms in acute inflammation: to resolve or not?; The American Journal of Pathology; 177(4); pp. 1576-1591; Oct. 2010.

Serhan; Novel pro-resolving lipid mediators are leads for resolution physiology; Nature; 510(7503); pp. 92-101; 24 pages; (Author Manuscript); Jun. 2014.

Cho et al.; Discovery of (2-fluoro-benzyl)-(2-methyl-2 phenethyl-2H-chromen-6-yl)-amine (KRH-102140) as an orally active 5-lipoxygenase inhibitor with activity in murine inflammation models; Pharmacology; 87(1-2); pp. 49-55; Feb. 2011.

Spite et al.; Resovins, specialized proresolving lipid mediators, and their potential roles in metabolic diseases; Cell Metabolism; 19(1); pp. 21-36; Jan. 7, 2014.

Srhan et al.; Resolving inflammation: dual anti-inflammatory and pro resolution lipid mediators, Nature Reviews Immunology; 8(5); pp. 349-361; 31 pages; (Author Manuscript); May 2008.

Stein et al.; Peripheral mechanisms of pain and analgesia; Brain Research Reviews; 60(1); pp. 90-113; 38 pages; (Author Manuscript); Apr. 2009.

Suleyman et al.; Anti-inflammatory and side effects of cyclooxygenase inhibitors; Pharmacological Reports; 59(3); pp. 247-258; May 2007.

Uddin et al.; Resolvins: natural agonists for resolution of pulmonary inflammation; Progress in Lipid Research; 50(1); pp. 75-88; 30 pages; (Author Manuscript); Jan. 31, 2011.

Vilcek: The cytokines; an overvew; In: Thomson WAaMTL, ed.: The Cytokine Handbook. 4 ed. San Diego: Academic Press, Calif, USA; pp. 1-18; (year of pub. sufficiently earlier than effective US filing date and any foreign priority date) 2012.

Wagener et al.; Different faces of the heme-heme oxygenase system in inflammation; Pharmacological Reviews; 55(3); pp. 551-571; Sep. 2003.

Wagener et al.; The heme-heme oxygenase system: a molecular switch in wound heaiing; Blood; 102(2); pp. 521-528; Jul. 15, 2003.

Wegiel et al.; Go green: the anti-inflammatory effects of biliverdin reductase; Frontiers in Pharmacology; 3; Article 47; doi: 10.3389/fphar.2012.00047; 8 pages; Mar. 16, 2012.

Xu et al.; Resolvins RvE1 and RvD1 attenuate inflammatory pain via central and peripheral actions; Nature Medicine; 16(5); pp. 591-597; 10 pages; (Author Manuscript); May 2010.

Yang et al., Metabolomics-lipidomios of eicosanoids and docosanoids generated by phagocytes, Current Protocols in Immunology; 95(1); pp. 14-26; 36 pages; (Author Manuscript); Nov. 2011.

Yang et al.; Reactive oxygen species in the immune system; International Reviews of Immunology; 32(3); pp. 249-270; Jun. 2013.

Yeretssian et al; Molecular regulation of inflammation and cell death; Cytokine; 43(3); pp. 380-390; Sep. 2008.

Babico; U.S. Appl. No. 17/080,815 entitled Current-based RF driver for pulsed electromagnetic field applicator systems, filed Oct. 26, 2020.

\* cited by examiner

FIG. 13A

HIGH-POWER PULSED ELECTROMAGNETIC FIELD APPLICATOR SYSTEM

CROSS REFERENCE TO RELATED APPLICATIONS

This application claims priority to U.S. Provisional Patent Application No. 62/536,409, filed Jul. 24, 2017, titled "HIGH-POWER PULSED ELECTROMAGNETIC FIELD APPLICATOR SYSTEM," which is herein incorporated by reference in its entirety.

The following U.S. patent applications are herein incorporated by reference in their entirety to the same extent as if each individual publication or patent application was specifically and individually indicated to be incorporated by reference: U.S. Pat. No. 6,334,069, titled "PULSED ELECTROMAGNETIC ENERGY TREATMENT APPARATUS AND METHOD," filed on Jan. 15, 1999, U.S. Pat. No. 6,353,763, titled "PULSED ELECTROMAGNETIC ENERGY TREATMENT APPARATUS AND METHOD," filed on Jun. 27, 2000, U.S. Pat. No. 6,967,281, titled "COVER FOR ELECTROMAGNETIC TREATMENT APPLICATOR." filed on Oct. 22, 2003, U.S. Pat. No. 6,974,961, titled "COVER FOR ELECTROMAGNETIC TREATMENT APPLICATOR," filed on Sep. 14, 2000, U.S. Pat. No. 7,024,239, titled "PULSED ELECTROMAGNETIC ENERGY TREATMENT APPARATUS AND METHOD," filed on Nov. 20, 2001, and PCT Patent Application No. PCT/US2015/062232, titled "TREATMENT OF CONDITIONS SUSCEPTIBLE TO PULSED ELECTROMAGNETIC FIELD THERAPY," filed on Nov. 23, 2015.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to pulsed electromagnetic field (PEMF) systems, apparatuses and methods. In particular, the disclosure relates to high-power pulsed electromagnetic field (PEMF) applicator systems.

BACKGROUND

Pulsed electromagnetic fields (PEMF) have been described for treating therapeutically resistant problems of both the musculoskeletal system as well as soft tissues. PEMF typically includes the use of low-energy, time-varying magnetic fields. For example, PEMF therapy has been used to treat non-union bone fractures and delayed union bone fractures. PEMF therapy has also been used for treatment of corresponding types of body soft tissue injuries including chronic refractory tendinitis, decubitus ulcers and ligament, tendon injuries, osteoporosis, and Charcot foot. During PEMF therapy, an electromagnetic transducer coil is generally placed in the vicinity of the injury (sometimes referred to as the "target area") such that pulsing the transducer coil will produce an applied or driving field that penetrates to the underlying tissue.

Treatment devices emitting magnetic and/or electromagnetic energy offer significant advantages over other types of electrical stimulators because magnetic and electromagnetic energy can be applied externally through clothing and wound dressings, thereby rendering such treatments completely non-invasive. Moreover, published reports of double blind placebo-controlled clinical trials utilizing a RF transmission device (Diapulse) suggest that this ancillary treatment device significantly reduces wound healing time for chronic pressure ulcers as well as for surgical wounds. Studies using Dermagen, a magnetic device manufactured in Europe which produces a low frequency magnetic field, have demonstrated significant augmentation of healing of venous stasis ulcers. Additionally, it has been shown that 50% fewer patients treated with electromagnetic energy develop reoccurring pressure ulcers, compared to control patients, suggesting that electromagnetic energy treatments impart some resistance to the reoccurrence of chronic wounds, such as pressure ulcers. Electromagnetic energy may also be useful as a preventative strategy. Analysis of the effects of electromagnetic energy on the treatment of pressure ulcers show that this treatment, by reducing healing time by an average of 50%, results in significant reductions in the costs associated with wound management.

Most PEMF transducers use a substantial amount of energy, and typically generate this energy in a base or controller portion, which may include batteries and/or a connection to a wall power source. The energy is typically conditioned or modulated into an appropriate signal and then transmitted (e.g., via a cable) to an applicator. This may make the systems expensive, and in some variations, heavy. The weight of the PEMF apparatus is generally proportional to the size of the power supply (in some cases, batteries) used to power the electrical circuitry as well as by the windings used to generate the output signal. Patient comfort while using such devices is often inversely proportional to the weight.

In particular, for high-power apparatuses (e.g., apparatuses that deliver over 40 W or greater than 100 V or energy), the generator portion is typically disposed in the base in a housing, and the pulsed high power electromagnetic energy is transferred to the applicator by a cable. This is conceptually simple, and allows efficient control of the energy to be applied. However, there are disadvantages, particularly when transferring high-energy signals on one or more cables.

Described herein are high-power PEMF applicator systems that may reduce high power electromagnetic energy leakage and may increase treatment efficiency.

SUMMARY OF THE DISCLOSURE

In general, described herein are high-power pulsed electromagnetic field (PEMF) applicator systems. These apparatuses (e.g., systems and devices) may include a base housing a controller that may couple to one or more applicators. The housing may generate a low-power signal (e.g., a low-voltage signal) that is received by one or more applicators and may be the basis for a high-power PEFM signal that is generated and emitted by the one or more applicators. Thus, although the one or more applicators are controlled by the base, the base generates a low power signal and the one or more applicators locally generate the high-power signal. The base generates the PEMF signal parameters and transmits this to the one or more applicators which then generate and apply the high power PEMF signal.

For example, a high-power PEMF signal system may include a base housing including a controller configured to generate a low-power control signal and one or more applicators coupled to the base. Each applicator can include a drive circuitry comprising a generator configured to receive the low-power control signal and to produce, in the applicator, a high-power, pulsed electromagnetic field signal based on the low-power control signal. The high-power pulsed electromagnetic field signal can have a power of greater than 40 W. Each applicator can further include a coil circuit configured to emit the high-power pulsed electromagnetic field signal, and an electromagnetic energy shield disposed between the drive circuitry and the coil circuit.

Any of the high-power pulsed electromagnetic field (PEMF) applicator system described herein may have one or more applicators, wherein the one or more applicators are configured to be hand-held.

Any of the applicators described herein may include a feedback circuit. For example, the apparatuses described herein may include a feedback circuit positioned behind the coil circuit and configured to detect the field strength of the high-power pulsed electromagnetic field signal emitted by the coil circuit. The controller may be configured to adjust an amplitude of the high-power pulsed electromagnetic field in response to the detected field strength by adjusting the low-power control signal. The feedback circuit may be printed on a first side of a printed circuit board and the coil circuit is printed on an opposite side of the printed circuit board.

In general, the high-power pulsed electromagnetic field signal may have an RF carrier frequency, such as a carrier frequency of about 27 MHz (e.g., 27.12 MHz, between about 10 MHz and 45 MHz, etc.).

Any of the applicators described herein may include a tuning/matching circuit. The tuning matching circuit may match the frequencies generated by the high-power generator on the applicator to the applicator coil.

In general, the controller (within the housing) may be configured to control operation of one, or more preferably, more than one, applicator apparatus. For example, a controller may include an energetic firmware configured to generate the low-power control signal. The low-power control signal may have a voltage equal or lower than 15 Volts. The low-power control signal may be encoded to indicate which of the one or more applicators the signal should be applied to. For example, an identifying code (e.g., 00, 01, 02, 03, etc.) may indicate which applicator to apply the signal being delivered.

The controller may be coupled to the one or more applicators by a cable. Alternatively, in some variations, the controller may be wirelessly coupled to the one or more applicators.

In general, the controller may wirelessly communicate with a remote processor (e.g., a remote server) to communicate prescription information specific to a particular user, performance behavior information about the apparatus (including error codes, etc.), firmware (and/or software) upgrades, patient compliance data, and the like. Any of these controllers may include a cellular module, configured to wirelessly communicate with a remote server.

The controller may also or alternatively include a diagnostic unit configured to run diagnosis and generate an error code. The controller may include a radio frequency identification (RFID) reader; alternatively or additionally, each applicator may include an RFID reader. An RFID signal may be used to indicate when an applicator (e.g., each applicator) is ready for operation, such as when a cover (e.g., drape, PEMF-transparent cover, etc.) is placed on the applicator permitting one or a limited/finite number time usage. Thus, the applicator may be disabled until a RFID tag is placed on the applicator, the RFID reader on the tag is read by the applicator, and the applicator is enabled to apply PEMF for a particular dose and/or period of time.

As mentioned, a low-power control signal may comprise an address unique to each of the one or more applicators. For example, the one or more applicator further comprises an address decoder.

In general, each applicator may include shielding to protect the circuitry forming the high-power generator (e.g., RF drive). For example, the at least one applicator further comprises a shield board configured to shield one side of the coil circuit. The shielding may be between the applicator coil and the circuitry. The applicator may include multiple shields. For example, applicator may include one or more shield "cans" or covers over the drive circuitry in addition to one or more shield boards behind the coil and/or the drive circuitry.

Any of the apparatuses described herein may include multiple applicators connected to the same base housing. The low-power base housing may then coordinate the applied PEMF signals to all of the applicators, including unlocking each one for use, transmitting a low-power signal targeted to each applicator (e.g., for coordinated delivery of PEMF energy, either in series or in parallel), etc. For example, each of the one or more applicator may comprise two or more generators and two or more coil circuits.

For example, described herein are high-power pulsed electromagnetic field (PEMF) applicator systems that include a base housing comprising a controller configured to generate a low-power control signal, wherein the controller is configured to include an applicator address in the low-power control signal, and a plurality of applicators coupled to the base. Each applicator can include a generator configured to receive the low-power control signal, decode the applicator address, and to produce, when the applicator address matches an identifying code corresponding to the applicator, a high-power, pulsed electromagnetic field signal based on the low-power control signal. The high-power pulsed electromagnetic field signal can have a power of greater than 40 W. Each applicator can include a coil circuit configured to emit the high-power pulsed electromagnetic field signal, and an electromagnetic energy shield disposed between the generator and the coil circuit.

In general, a high-power pulsed electromagnetic field (PEMF) applicator can include a drive circuitry configured to receive a low-power control signal from a controller, wherein the drive circuitry comprises a generator configured to generate high-power pulsed electromagnetic field signal having a power of 40 W or greater based on the low-power control signal. The applicator can include a coil circuit configured to apply the high-power pulsed electromagnetic field signal to a subject, an electromagnetic energy shield disposed over the drive circuitry, and a detector configured to detect a field strength of the high-power pulsed electromagnetic field signal applied by the coil circuit, wherein the detector is configured to transmit the field strength to the controller so that the controller can adjust the low-power control signal in response to the detected field strength.

A detector may be disposed on an opposite side of a printed circuit board from the coil circuit to prevent capacitive coupling.

As mentioned, the generator may be configured to generate pulsed radio frequency (RF) electromagnetic energy having a carrier frequency of between 10 MHz and 45 MHz (e.g., 27 MHz, 27.12 MHz, etc.).

The controller (housing) may signal to each applicator using an identifying address. Thus, the applicator may further include an address decoder. For example, the applicator can include an input from the cable including a local (applicator) controller/processor which may include circuitry for receiving the control signal from the base. The controller/processor in the applicator may be part of or connected with the RF drive (e.g., generator) and may help form the high-power signal from the low-power signal received from the base.

As mentioned, the applicator may be configured to shield and/or direct the PEMF signal emitted by the coil in the applicator. In particular, the circuitry in the applicator (the high-power generator/RF drive) may be shielded. The applicator may include a shield board configured to allow the electromagnetic energy to emit primarily in one direction and for improving EMI performance (e.g. preventing electromagnetic interference). The applicator can further include an antenna board.

Also described herein are methods for treating a patient with high-power pulsed electromagnetic fields using any of the apparatuses described herein. Generally, any of these methods may include transmitting low-power signal from a base to which one (or more preferably, more than one) applicator is coupled and locally, in the applicator, generating a high-power (e.g., >40 W, >45 W, >50 W, >55 W, >60 W, etc. and/or >100V, >120V, >140V, >150V, >175V, >200V, etc.). The methods can include providing a low-power control signal including a gating code from a controller in a base housing, transmitting the low-power control signal to at least one hand-held applicator in communication with the base housing, generating, in the hand-held applicator, a high-power, pulsed electromagnetic field signal based on the low-power control signal when the gating code matches an identifier code for the hand-held applicator, emitting the high-power, pulsed electromagnetic field signal from a coil in the at least one applicator, and detecting the emitted high-power, pulsed electromagnetic field signal using a detector that is coupled to an opposite side of the coil in the hand-held applicator.

For example, the methods described herein can further include the step of transmitting the low-power control signal having 15V or lower. The methods can further include the step of adjusting the low-power control signal based on the detected emitted high-power, pulsed electromagnetic field signal (e.g., based on feedback detected from the applicator).

The methods described herein can further include running diagnosis and generating an error code in the base housing. These codes may be stored, displayed, and/or transmitted (e.g., to a remote server) for action by the remote server, including sending a replacement, or transmitting software/firmware fix/update information to the base housing. Generally, the methods described herein can include the step of wirelessly receiving, in the base housing, instructions from a remote server.

Any of the methods described herein can further include the step of transmitting the low-power control signal to a plurality of hand-held applicators.

In general, any of the methods described herein may include metering or controlling the delivery based on a prescription or metering device. For example, the methods described herein can include the step of transmitting a radio frequency identification (RFID) address between the hand-held applicator and the base housing. The hand-held applicator may generate the high-power, pulsed electromagnetic field only after the base housing verifies the RFID address.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

in FIG. 11A, the board is populated with electronic components that may control the applicator (e.g., the coil antenna).

FIG. 13A illustrates an example of simulation parameters of an applicator for a high-power pulsed electromagnetic field (PEMF) applicator system.

DETAILED DESCRIPTION

The present disclosure now will be described in detail with reference to the accompanying figures. This disclosure may be embodied in many different forms and should not be construed as limited to the example embodiments discussed herein.

Described herein are high-power pulsed electromagnetic field (PEMF) applicator systems. The systems can comprise a base housing including a controller configured to generate a low-power control signal and one or more applicators coupled to the base. Each applicator can include a drive circuitry comprising a generator configured to receive the low-power control signal and to produce a high-power, pulsed electromagnetic field signal based on the low-power control signal, in the applicator instead of in the base housing. The high-power pulsed electromagnetic field signal can has a power of greater than 40 W. It is advantageous for the generator to be disposed in the applicator instead of in the base housing. When the generator is disposed in the base housing, the high power electromagnetic field signal is transmitted to the applicator by a cable. There may be leakage of electromagnetic field signal from the base housing and from the cable, which can be harmful to the patients, and have negative effects for other circuitry in the base housing as well. It is difficult to shield the leakage from the base housing and from the cable. When the generator is disposed in the applicator, the high power electromagnetic field signal is generated in the applicator locally. There will not be high power electromagnetic field signal in the base housing and in the cable, thus significantly reducing harmful electromagnetic field signal leakage and increasing treatment efficiency.

Each applicator can further include a coil circuit configured to emit or apply the high-power pulsed electromagnetic field signal. Since the high power electromagnetic energy is generated locally in the applicator, an electromagnetic energy shield is disposed in the applicator between the drive circuitry and the coil circuit to prevent the drive circuit from the high power electromagnetic energy. For example, the electromagnetic energy shield can be disposed over the drive circuitry on the applicator to shield the emission of the electromagnetic energy.

Figure 1:
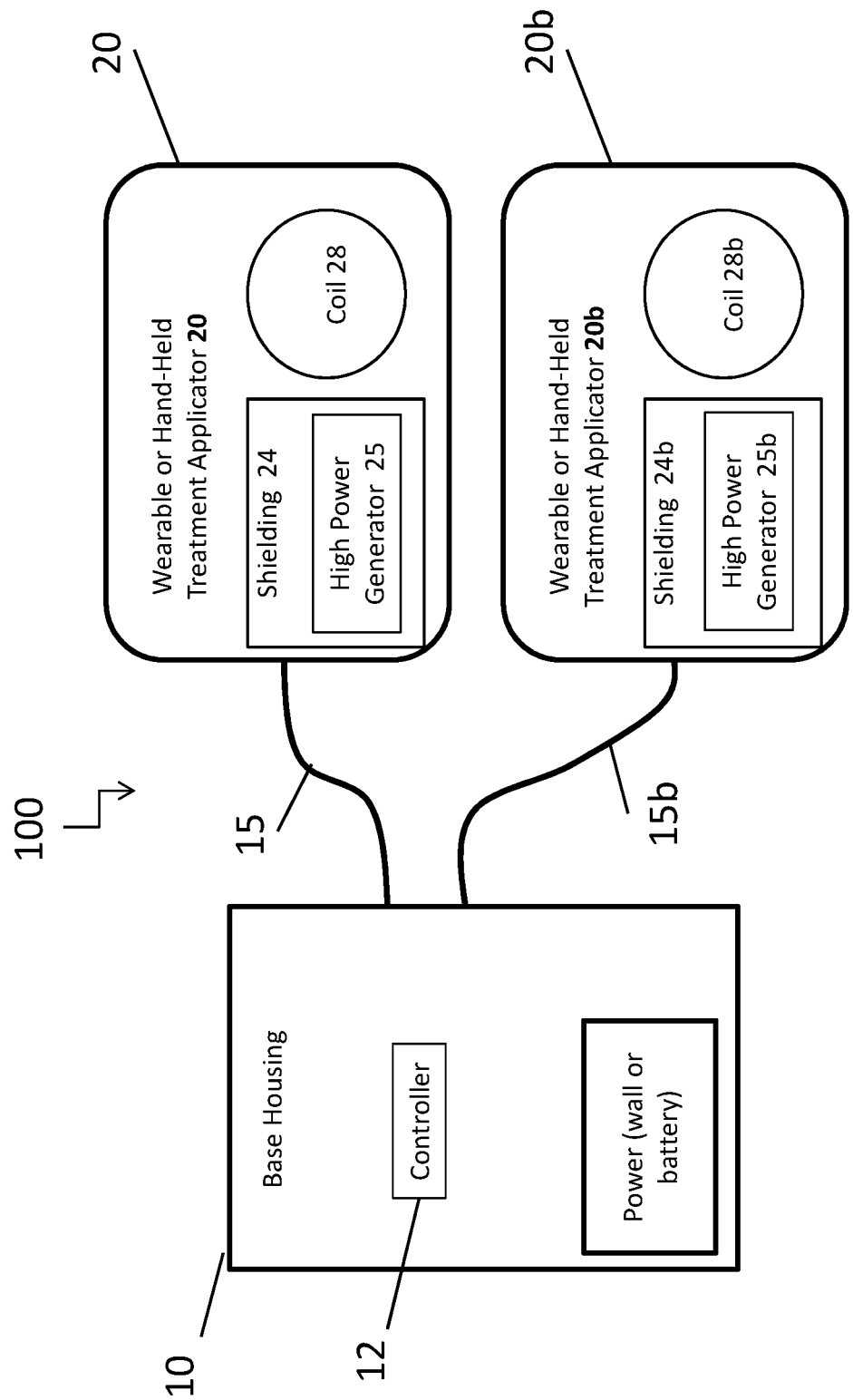
FIG. 1 schematically illustrates one example of a schematic of a high-power pulsed electromagnetic field (PEMF) applicator system according to one embodiment of the disclosure.

FIG. 1 schematically illustrates one example of a schematic of a high-power pulsed electromagnetic field (PEMF) applicator system 100 in one embodiment. As shown in FIG. 1, the systems 100 can include a base housing 10 including a controller 12 configured to generate a low-power control signal and one or more applicators, (e.g., 20, 20b) coupled to the base housing 10. For example, the base housing 10 is coupled to the one or more applicators (e.g., 20, 20b) by one or more cables (e.g., 15, 15b). For example, two applicators 20 and 20b are shown in FIG. 1, where the base housing 10 is coupled to the two applicators 20 and 20b by two cables 15 and 15b. In some variations, the base housing 10 is coupled to the two applicators 20 and 20b wirelessly.

Each applicator (e.g., 20, 20b) can include a drive circuitry comprising a generator (e.g., 25, 25b) configured to receive the low-power control signal and to produce a high-power, pulsed electromagnetic field signal based on the low-power control signal, in the applicator instead of in the base housing. The high-power pulsed electromagnetic field signal can have a power of greater than 40 W. The applicator (e.g., 20, 20b) can have a high voltage set-up locally, while the base housing 10 and the one or more cables (e.g., 15, 15b) remain low voltage. When the generator (e.g., 25, 25b) is disposed in the applicator (e.g., 20, 20b), the high power electromagnetic field signal is generated in the applicator locally, thus significantly reducing harmful electromagnetic field signal leakage and increasing treatment efficiency.

Each applicator can further include a coil circuit (e.g., 28, 28b) configured to emit or apply the high-power pulsed electromagnetic field signal. Since the high power electromagnetic energy is generated locally in the applicator, an electromagnetic energy shield (e.g., 24, 24b) is disposed in the applicator between the drive circuitry and the coil circuit, for example, over the drive circuitry on the applicator to shield the circuitry from the emission of the high power electromagnetic energy.

For example, the one or more applicators can be configured to be hand-held or wearable for the convenience of treatment. The one or more applicators can be applied to the back, the feet, the hand, the shoulder, or any other parts of the body of the patient.

Figure 2:
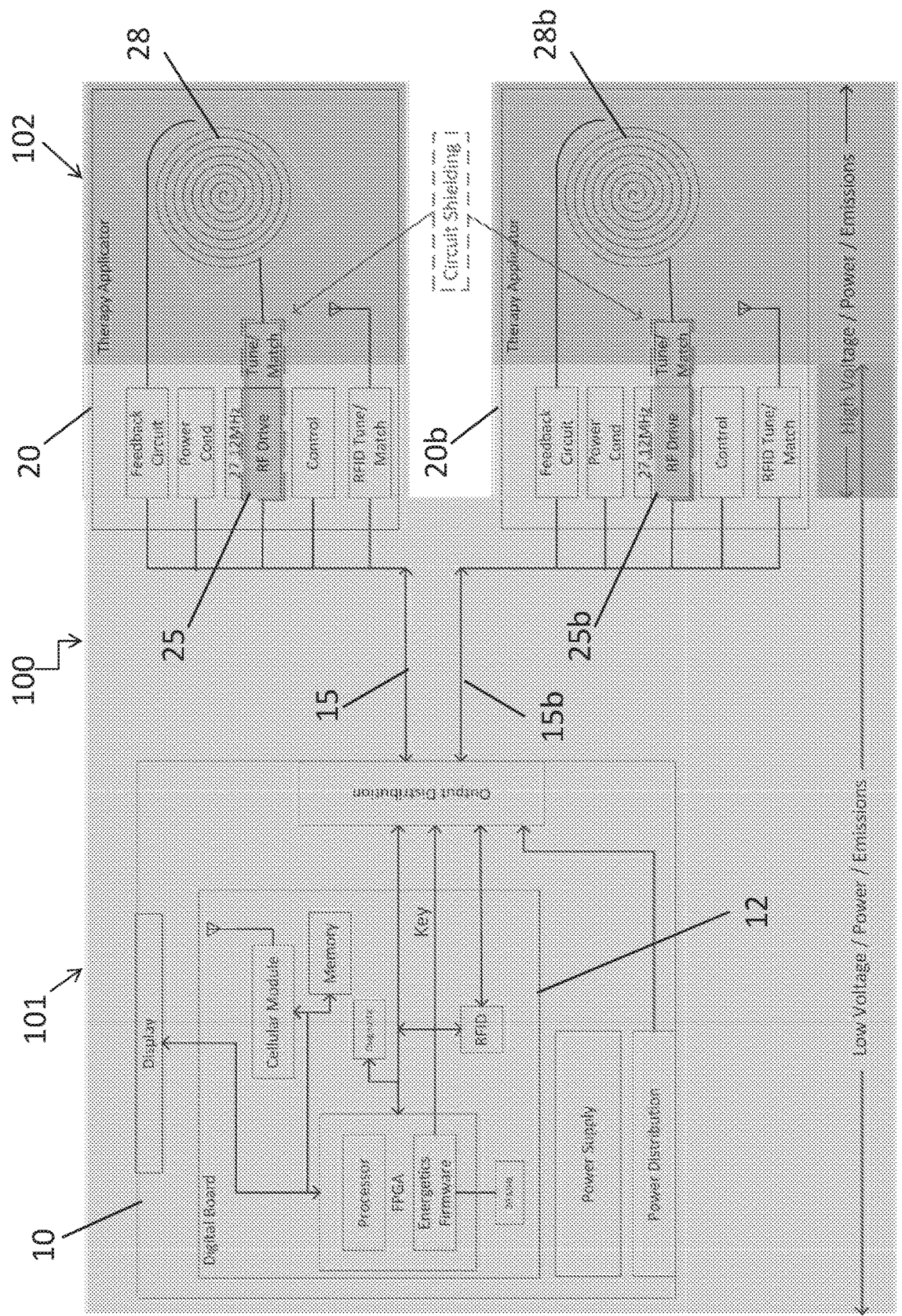
FIG. 2 schematically illustrates an example of a block diagram of a high-power pulsed electromagnetic field (PEMF) applicator system.

FIG. 2 schematically illustrates an example of a block diagram of the high-power pulsed electromagnetic field (PEMF) applicator system 100. The block diagram includes a first section 101 and a second section 102. The first section 101 is a low power section including the base housing 10, the one or more cables 15, 15b and a low power portion of the one or more applicators 20, 20b. The second section is a high power section portion of the one or more applicators 20, 20b including the generators 25, 25b and the coil circuits 28, 28b.

As shown in FIG. 2, the applicator s 20, 20b can include the generator 25, 25b. For example, in some variations, the generators 25, 25b are configured to generate high power radio frequency (RF) electromagnetic field. For illustration only, the generator is also referred as RF drive in this disclosure. However, it is understood that the generator is not limited to RF drive. The applicators 20, 20b can also include one or more tuning/matching circuits.

For example, for RF circuitry, a high power means a power of 40 W or higher. As shown in FIG. 2, the base housing 10, the cables 15, 15b and a portion of the applicators 20, 20b are low power, for example, really small <0.01 W. In the generator, for example, the RF drive, the power can be boosted to 40 W. In terms of voltages, the base housing 10, the cables 15, 15b and a portion of the applicators 20, 20b have low-voltage signals, for example, about 3 Volts or 15 Volts. For example, the low-power control signal has a voltage equal or lower than 15 Volts. The high power portion including the generators and the coil circuits have high voltage signals, for example, about 200 Volts.

The base housing 10 can include a controller 12. The controller 12 can include a processor, for example, an embedded microprocessor to increase the capability of the system. For example, the controller can comprise an energetic firmware configured to generate the low-power control signal. For example, the controller 12 can include a FPGA block in addition to an energetics firmware. The base housing can further include a display. The base housing 10 can have a user interaction interface and programmable functionalities.

For example, in some variations, the controller 12 can have a cellular module, which can be configured to communicate with a server wirelessly and monitor compliance remotely. The controller 12 can further include a memory unit to store data on the system.

For example, the controller 12 can further comprise a diagnostic unit configured to run diagnosis and generate an error code. For example, the diagnosis unit can be configured to run a diagnosis on the system 100 when the system is power up. The diagnostic info (and compliance/use info, etc.) can be displayed in the display. When the diagnosis unit detects a problem, the diagnosis unit can generate and display an error code. For example, the error code can be stored in the memory of the controller 12. For another example, when there is a cellular module, the system 100 can make connection with the cellular network and upload the diagnostic info (and compliance/use info, etc.) from prior use. The diagnostic info can be sent to the server, along with a unique ID for the system.

Figure 3:
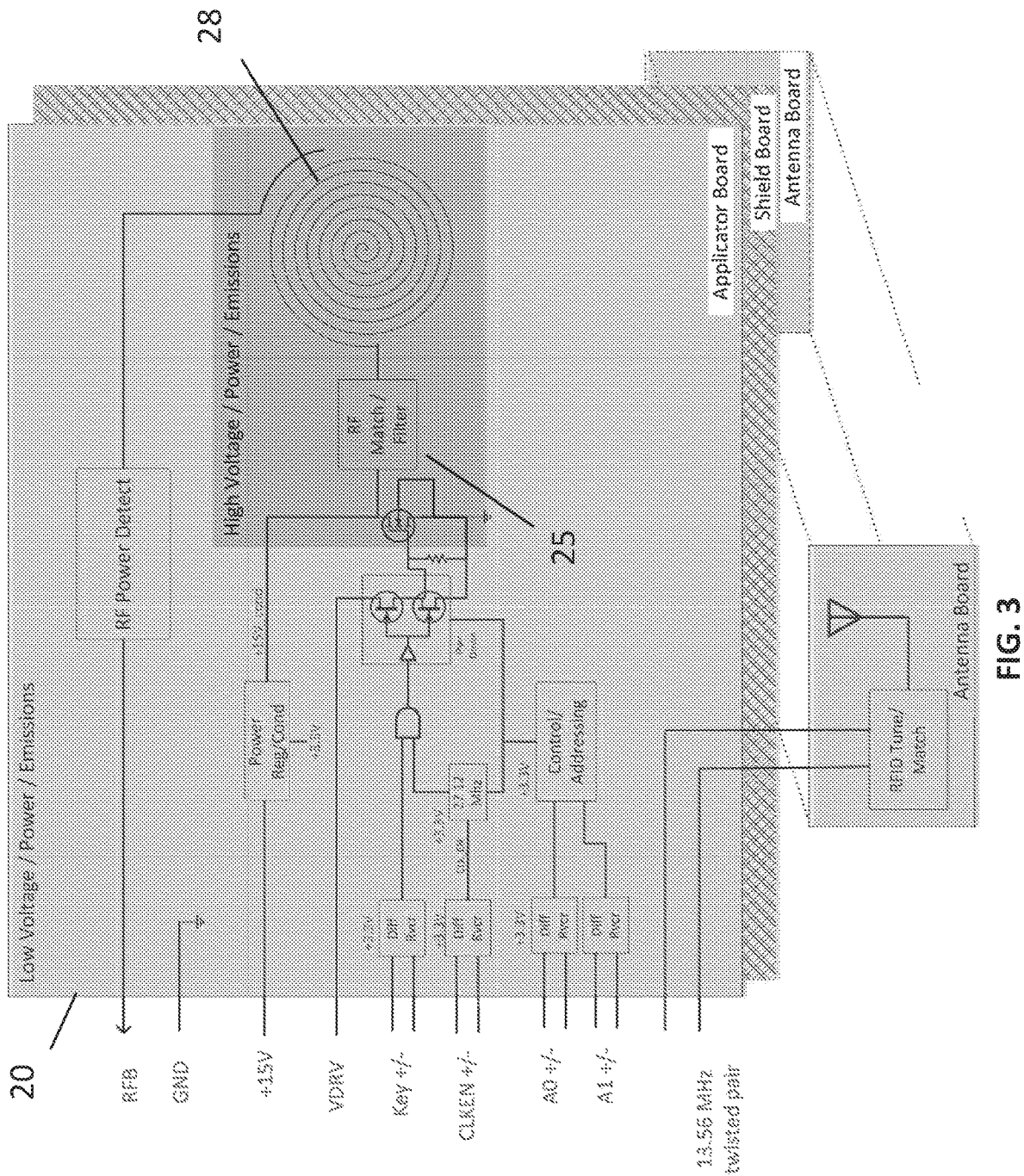
FIG. 3 schematically illustrates further details of an applicator in a high-power pulsed electromagnetic field (PEMF) applicator system.

For example, each of the one or more applicators can have a unique radio frequency identification (RFID) tag. For example, the controller 12 can further comprise a radio frequency identification (RFID) reader. The radio frequency identification (RFID) can be transmitted through the one or more cables to RFID Tune/Match in the one or more applicators as shown in FIG. 3. The antenna is co-located with RFID tag in the one or more applicators. When the user presses "start therapy" on the system, the radio frequency identification (RFID) reader will automatically (as initial routine) read RFID tag on each applicator; if the radio frequency identification (RFID) reader determines the RFID tag fails, the controller is configured to not allow to proceed with the treatment. Indication of failure of RFID is on display as well.

For example, the one or more applicator comprises two or more applicators. For example, the low power control signal can comprise an address unique to each of the one or more applicators. For example, the one or more applicator further comprises an address decoder. The low power control signal can be transmitted to the one or more applicator with an address, only the applicator that matches the address can be turned on. In this way, the one or more applicators can be turned time sequentially.

In some variations, the system can be wireless with battery operated applicators. The controller could be battery operated (low power). Because the carrier frequency is generated in the applicator, the transmission of data is simplified.

FIG. 3 schematically illustrates details of the applicator 20 in the high-power pulsed electromagnetic field (PEMF) applicator system 100. For example, the high-power pulsed electromagnetic field signal has a carrier frequency of about 27 MHz. For example, each applicator of the one or more applicators can further comprise a tuning/matching circuit. The applicator 20 can further include a shield to protect the lower power portion in the applicator from the high power electromagnetic field emission of the coils 28.

Figure 6:
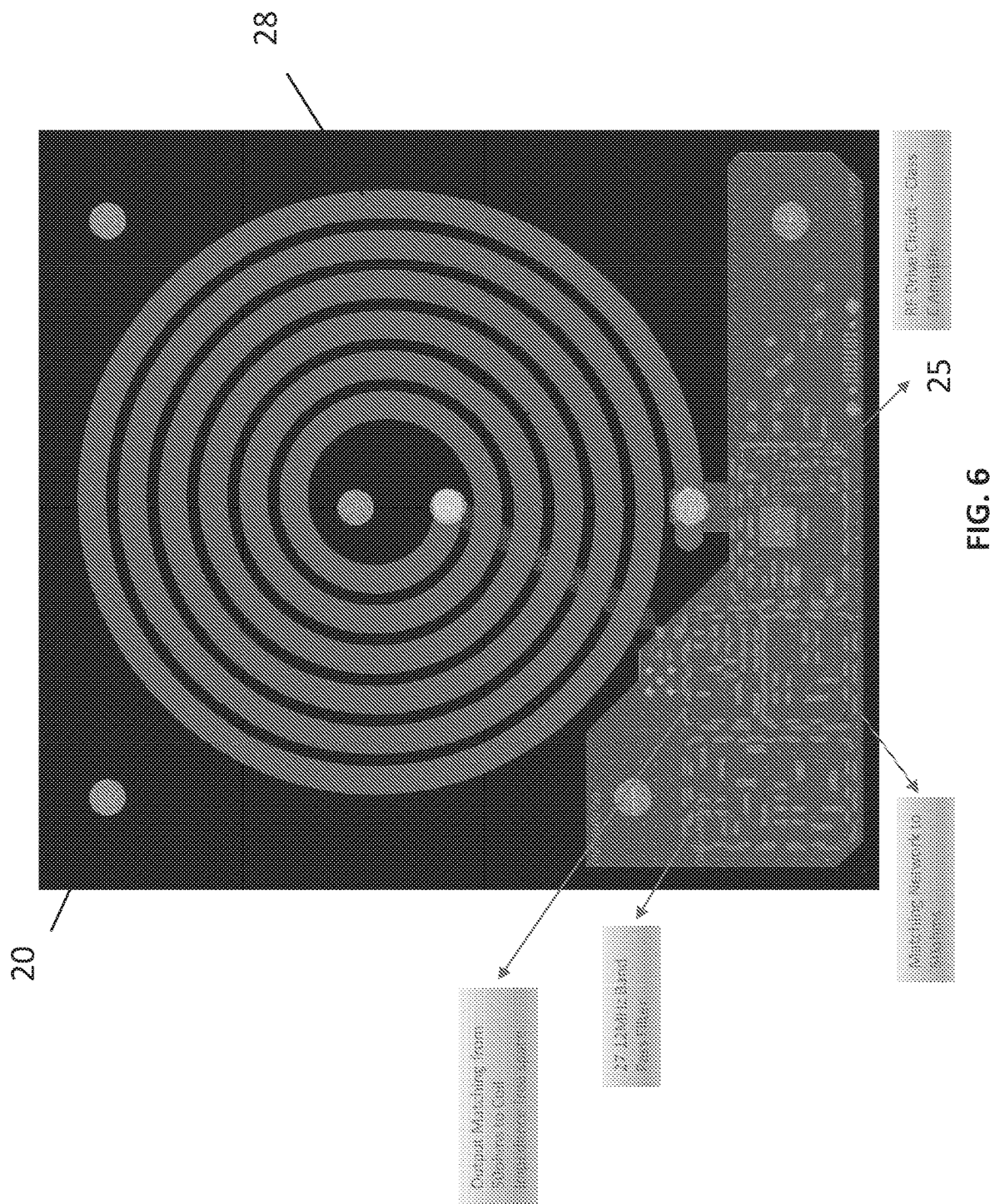
FIG. 6 illustrates an example of a top view of circuit layout of an applicator for a high-power pulsed electromagnetic field (PEMF) applicator system.

FIG. 6 illustrates an example of a top view of circuit layout of the applicator 20 in the high-power pulsed electromagnetic field (PEMF) applicator system 100. The applicator circuitry can include the generator 25, RF drive. The applicator can further include a band pass, a first matching network and a second matching network. The matching networks are necessary for impedance match. For example, the first matching network can be configured to match network for 50 Ohm impedance. The second matching network can be configured for output matching from 50 Ohm to coil impedance free space.

As shown in FIG. 6, the applicator can include the shield to protect the lower power portion from the high power electromagnetic field emission. For example, the shield can include four shielded areas inside the four rectangle areas to protect the four segments of the circuitry: the RF drive, the band pass filter, the first and the second matching networks.

Referring to FIG. 3 and FIG. 6, each of the one or more applicator can comprise a feedback circuit positioned behind the coil circuit and configured to detect a field strength of the high-power pulsed electromagnetic field signal emitted by the coil circuit and send back the detected field strength to the controller in the base housing. For example, the controller is configured to adjust an amplitude of the high-power pulsed electromagnetic field in response to the detected field strength by adjusting the low-power control signal, thereby achieving a constant level of field strength. U.S. Pat. No. 6,334,069 discloses details of the feedback circuit.

In some variations, the feedback circuit is printed on a first side of a printed circuit board and the coil circuit is printed on an opposite side of the printed circuit board. When the feedback circuit is printed on the same side of the coil circuit, there is a problem of capacitive coupling to the coil circuit. For example, even though the field strength is decreasing, the measured field strength can be still high because of capacitive coupling, thus resulting inaccurate measurement. By printing the feedback circuit on the opposite side of the coil circuit, capacitive coupling is eliminated. Therefore, it is advantageous to print the feedback circuit on the opposite side of the coil circuit to increase measurement accuracy by eliminating capacity coupling errors.

In some variations, the applicator further comprises a shield board configured to shield one side of the coil circuit. The shield board only allows the electromagnetic field goes in one direction. The applicator can further include an antenna board for RFID tuning and matching.

Figure 4:
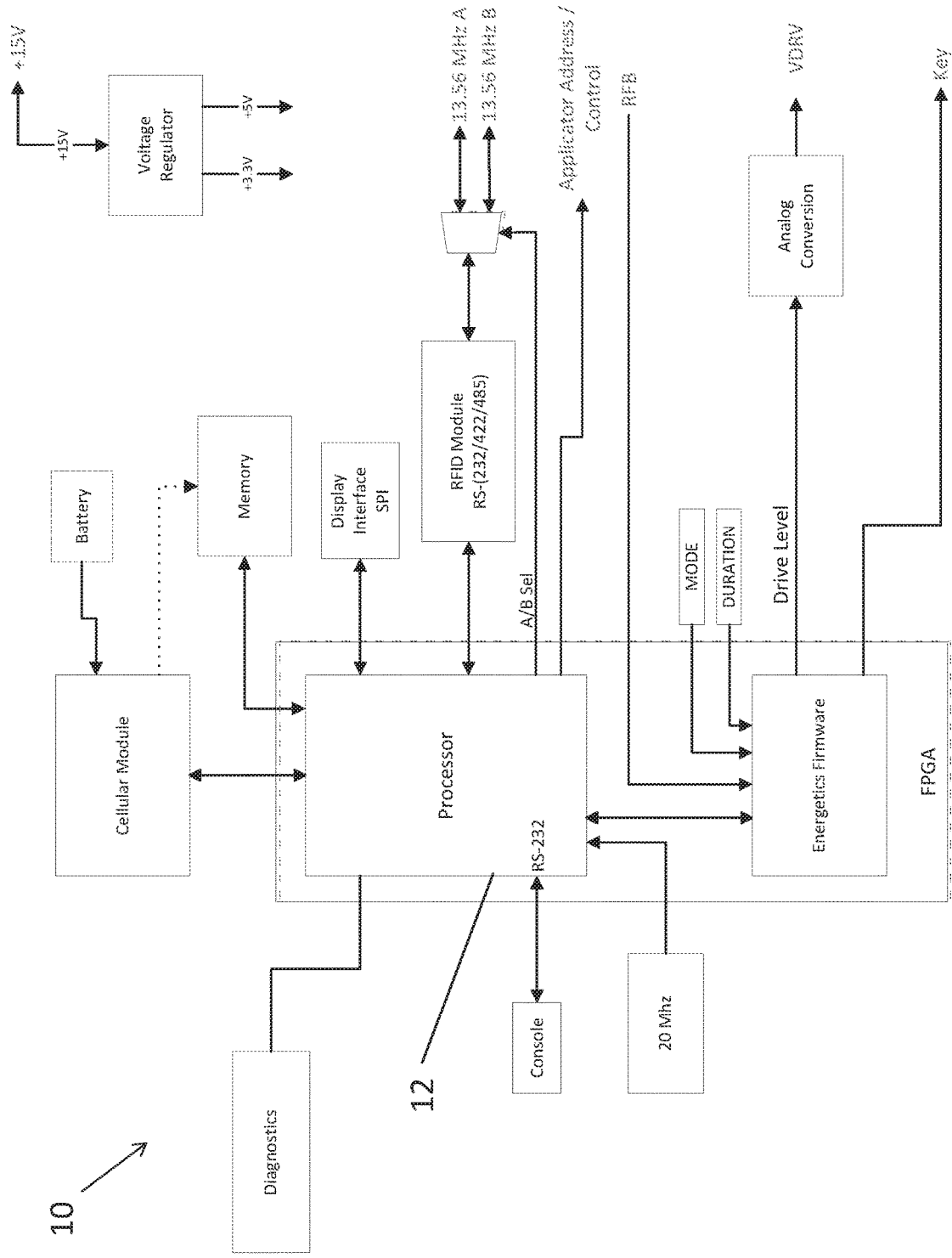
FIG. 4 schematically illustrates further details of a base housing in a high-power pulsed electromagnetic field (PEMF) applicator system.
Figure 5:
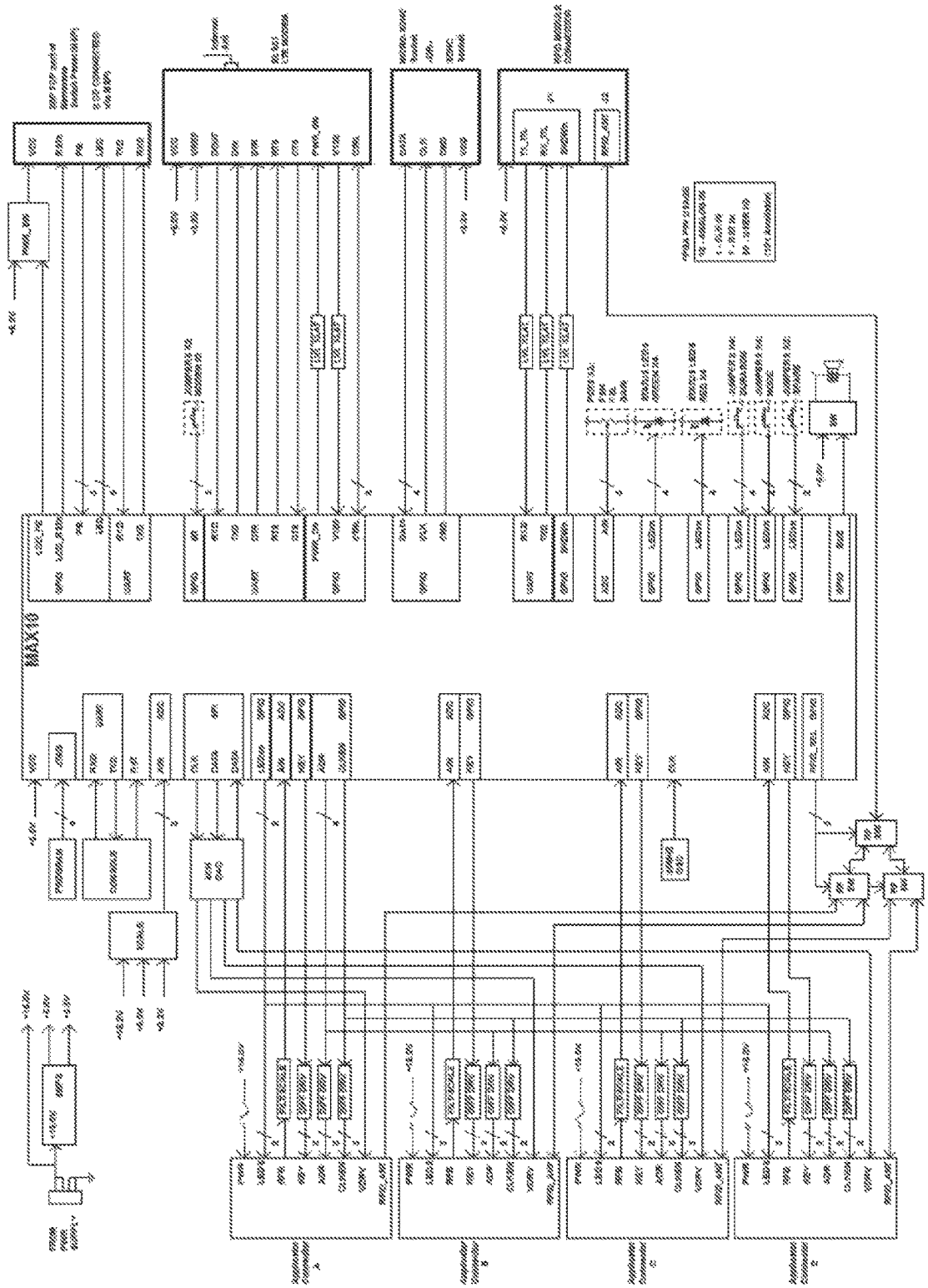
FIG. 5 schematically illustrates one example of circuit design of a high-power pulsed electromagnetic field (PEMF) applicator system.

FIG. 4 schematically illustrates further details of a base housing 10 in the high-power pulsed electromagnetic field (PEMF) applicator system. The energetic firmware can be configured to generate a gating signal to turn on the one or more applicator s.

For example, the gating signal sent to the one or more applicators can be identical. However, the gating signal can be configured to include an address. The one or more applicators receive the same address. Each of the one or more applicators has its own unique address. Each of the one or more applicators has an address decoder. Only the address of one of the one or more applicators matches the address in the gating signal at one time, thus only one applicator is turned on at one time.

In the case of two applicators, for example, the first applicator 20 can have an address of "00", and the second applicator 20 can have an address of "01". The controller can be configured to send a first gating signal including the address of "00". The first applicator 20 is addressed. The first applicator 20 takes the pulse and gates through the carrier frequency. Then controller can be configured to send a second gating signal including the address of "01". The second applicator 20b is addressed. The second applicator 20 takes the pulse and gates through the carrier frequency.

After the applicator gates the carrier frequency, the signal goes into the generator, for example, RF drive, where the signal is boosted to high power level. For example, a class-E amplifier can be used in the RF drive, which is very high efficiency.

Figure 7:
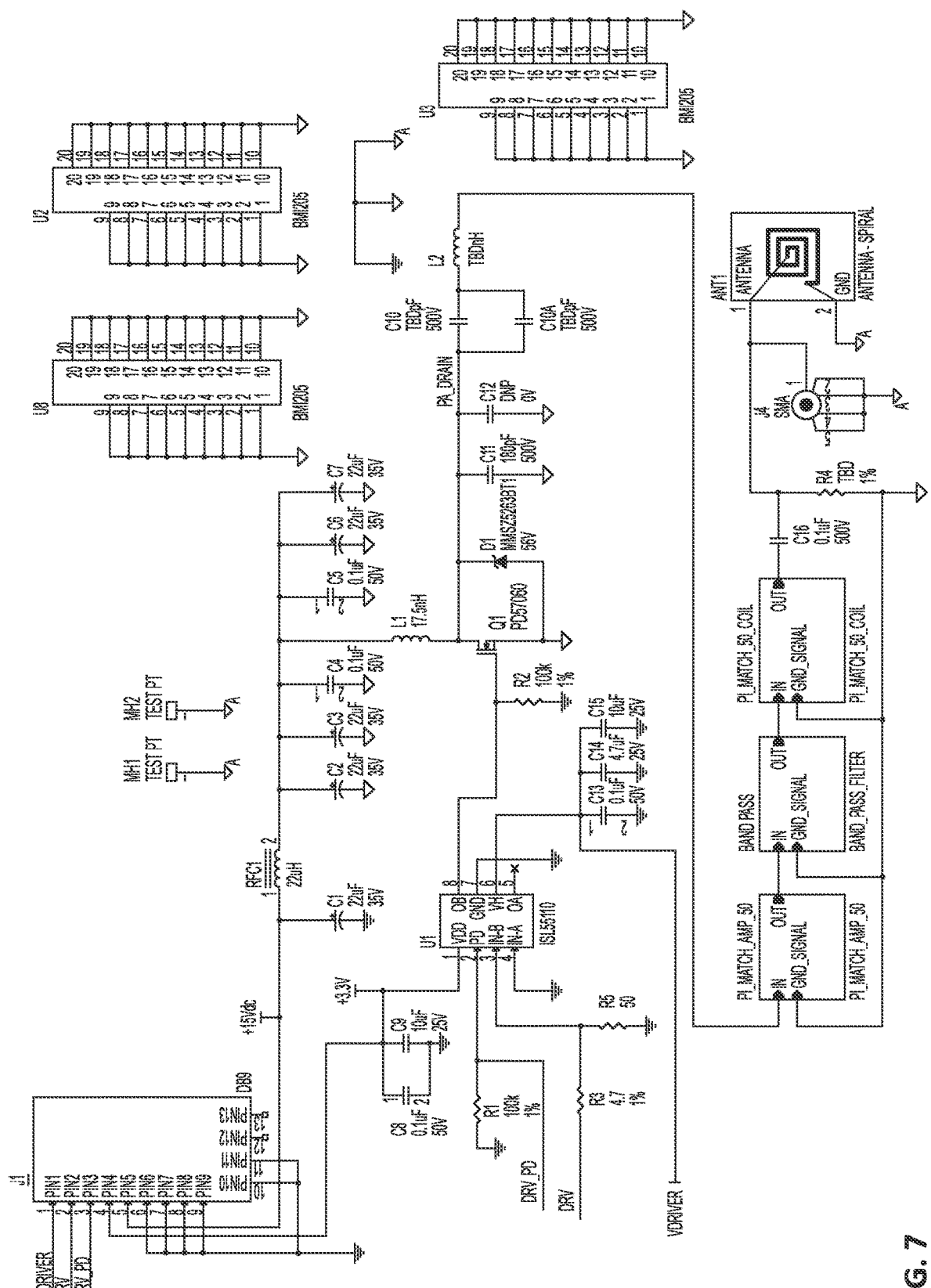
FIG. 7 illustrates one example of a portion of circuit design of a high-power pulsed electromagnetic field (PEMF) applicator system.

FIG. 7 illustrates one example of a portion of circuit design of the high-power pulsed electromagnetic field (PEMF) applicator system. When the signals pass through the coil circuit, the coil circuit generates the electromagnetic field. When the patient brings a body part to be treated in the range of the electromagnetic field, the body part becomes a part of the circuit, thus the electromagnetic field power being delivered to the body part to perform the treatment. As shown in FIG. 7, the applicator can include the generator/RF drive, for example, which can be a power amplifier that converts 15 V voltage to 200 V or more voltage. As discussed above, the applicator can include a first network and a second matching network. For example, the first matching circuit coverts the amplifier impedance to 50 ohm impedance. 50 Oms is standard in the industry is standard for RF energy. This is the entire reason you need a match. The bandpass filter limits the carrier frequency to just 27 MHz. The second matching circuit matches the impedance of the coil circuits. Without impedance matching, the power transfer is low-efficiency, which might result in overheating of the electronics. When the impedance matches, the power transfer is high-efficiency. It is advantageous to match impedance to maximize the power transfer.

Figure 8:
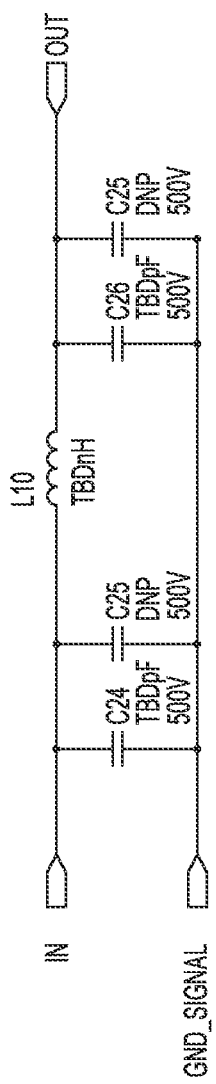
FIG. 8 illustrates one example of a first matching network in a circuit design for a high-power pulsed electromagnetic field (PEMF) applicator system.
Figure 9:
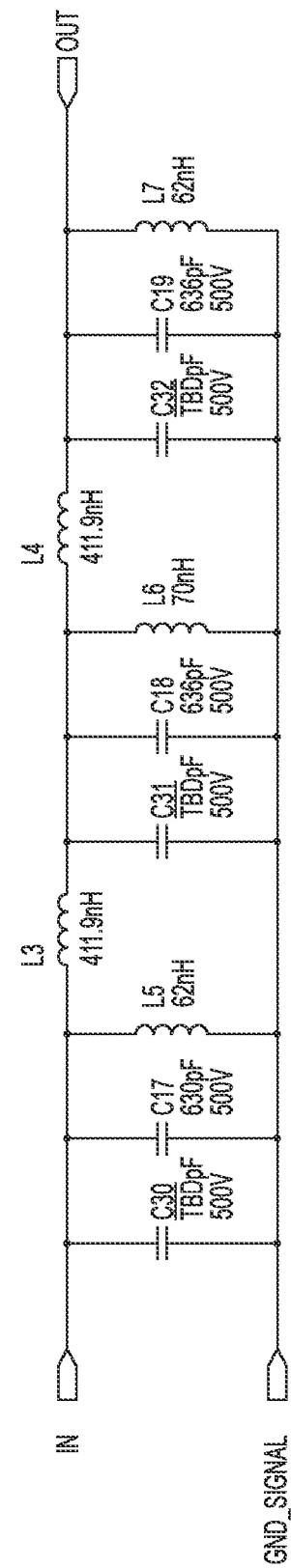
FIG. 9 illustrates one example of a band pass filter in a circuit design of a high-power pulsed electromagnetic field (PEMF) applicator system.
Figure 10:
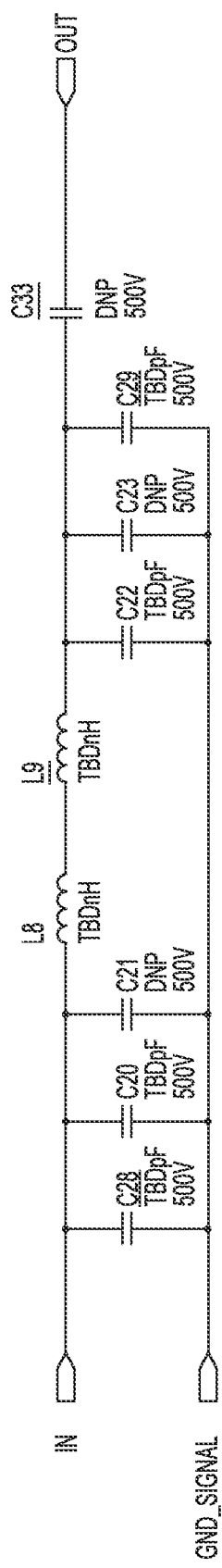
FIG. 10 illustrates one example of a second matching network in a circuit design of a high-power pulsed electromagnetic field (PEMF) applicator system.

FIG. 8 illustrates one example of a first matching network in the circuit design of the high-power pulsed electromagnetic field (PEMF) applicator system. FIG. 9 illustrates one example of a band pass filter in the circuit design of the high-power pulsed electromagnetic field (PEMF) applicator system. FIG. 10 illustrates one example of a second matching network in the circuit design of the high-power pulsed electromagnetic field (PEMF) applicator system.

Figure 11B:
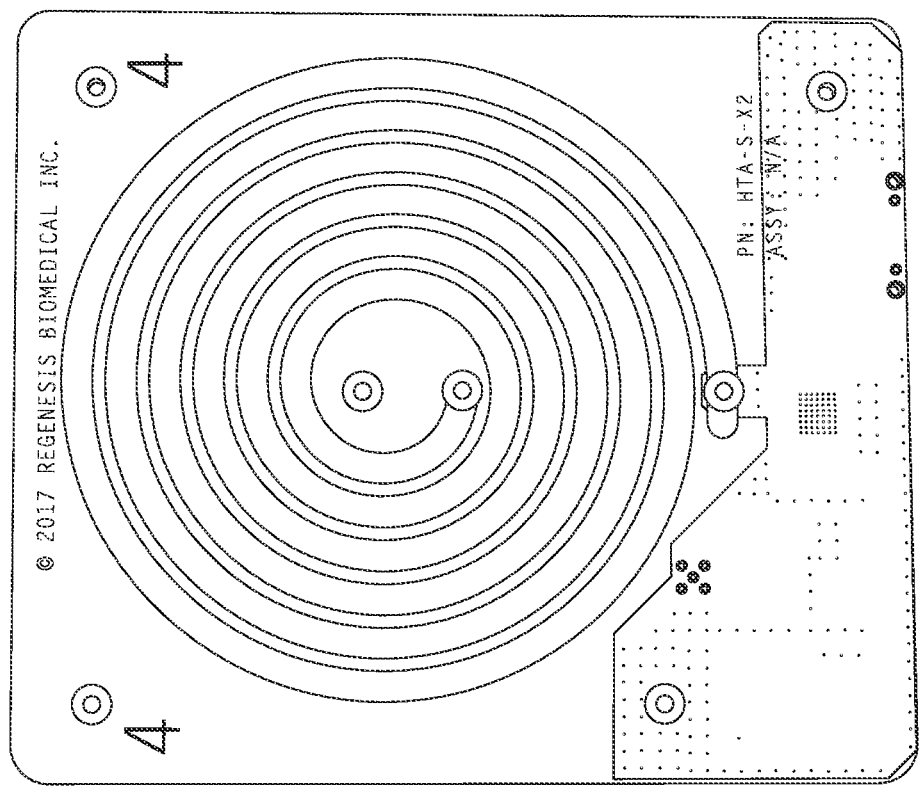
FIG. 11B illustrates an example of a top view of the circuit board of an applicator in a high-power pulsed electromagnetic field (PEMF) applicator system when the board is unpopulated.
Figure 11A:
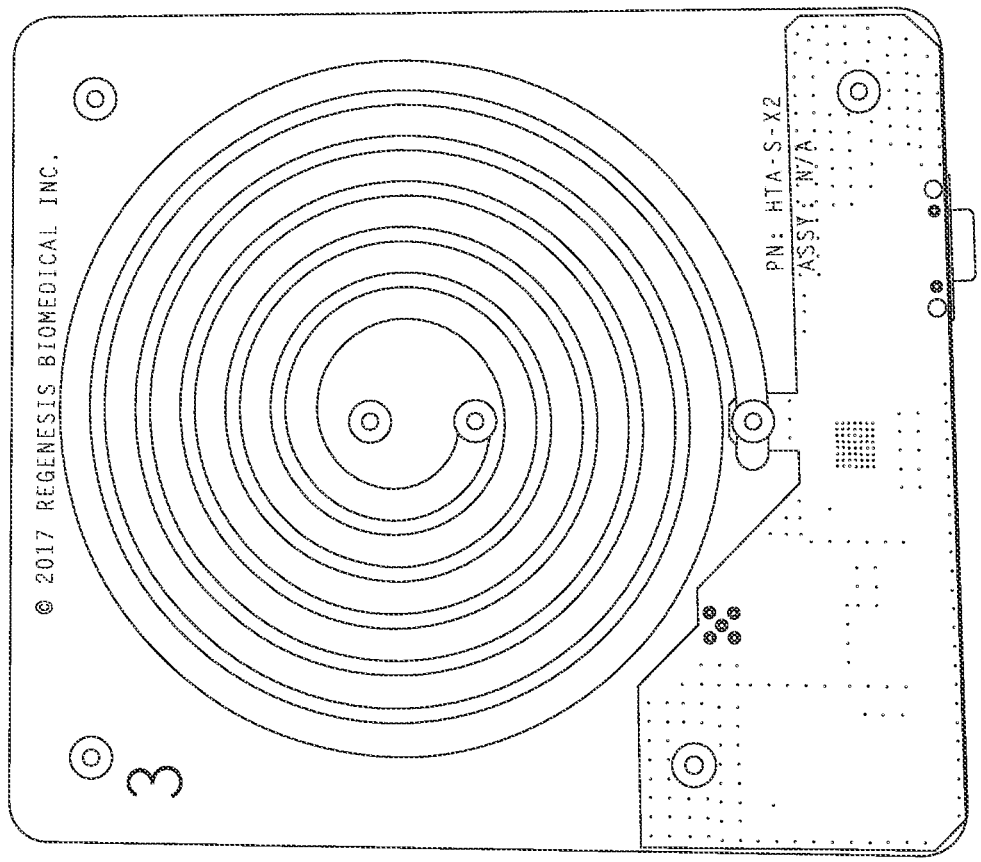
FIG. 11A illustrates an example of a top view of a circuit board of an applicator in the high-power pulsed electromagnetic field (PEMF) applicator system such as the one shown in FIG. 1.
Figures 12A, 12B:
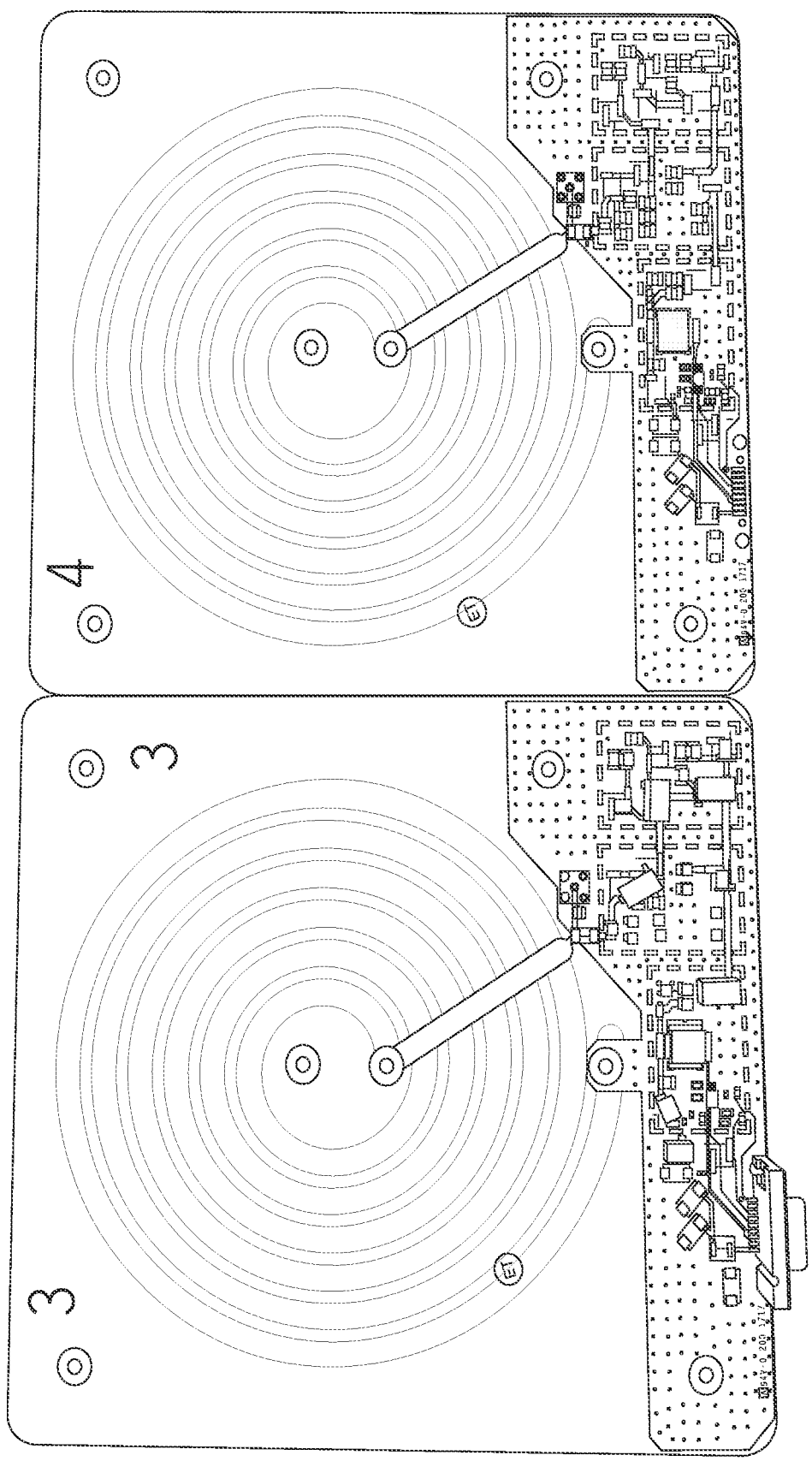
FIG. 12A illustrates an example of a back view of a circuit board of FIG. 11A, showing the circuitry for the applicator of a high-power pulsed electromagnetic field (PEMF) applicator system such as the system of FIG. 1.
FIG. 12B illustrates an example of a back view of a circuit board of an applicator such as the one shown in FIG. 11B.

FIG. 11A illustrates an example of a top view of a circuit board of an applicator in a high-power pulsed electromagnetic field (PEMF) applicator system such as the one shown in FIG. 1, when the board include electronic components that may regulate the activity of the apparatus. FIG. 12A is an example of a back view of the same board. FIG. 1B illustrates an example of a top view of a circuit board of an applicator in the high-power pulsed electromagnetic field (PEMF) applicator system in FIG. 1 when the board is unpopulated. FIG. 12B is an example of a back view of the board shown in FIG. 11B.

In FIGS. 11A and 12A, the board may include a drive circuitry including, for example, a generator configured to receive the low-power control signal and to produce, in the applicator, a high-power, pulsed electromagnetic field signal based on the low-power control signal. In some variations, the generator is configured so that the high-power pulsed electromagnetic field signal has a power of greater than 40 W. FIG. 11A also shows an example of a coil circuit configured to emit the high-power pulsed electromagnetic field signal. An electromagnetic energy shield may be disposed between the drive circuitry and the coil circuit.

Figure 12C:
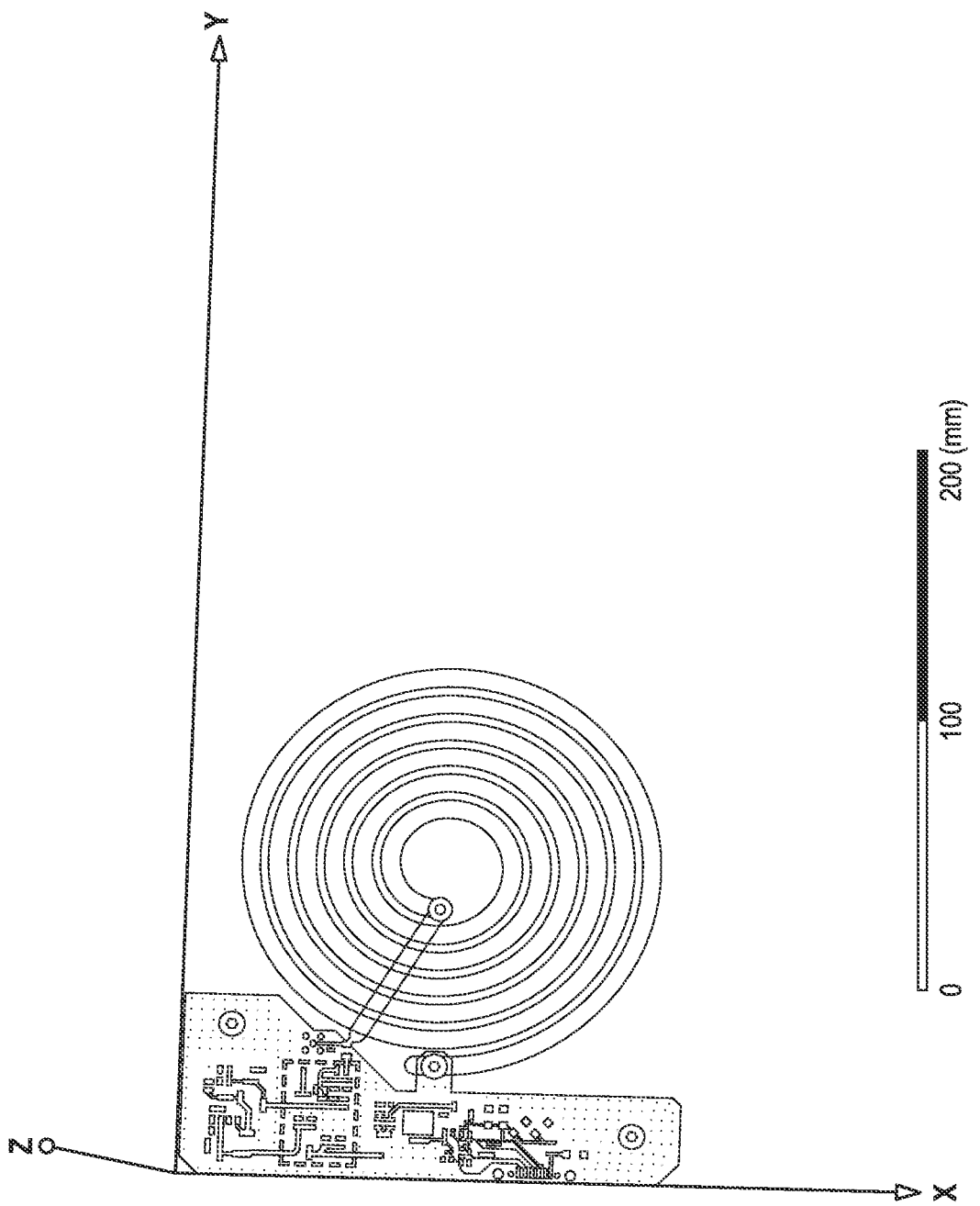
FIG. 12C illustrates an example of a circuit layout schematic of an applicator in the high-power pulsed electromagnetic field (PEMF) applicator system in simulation software.
Figure 13A:
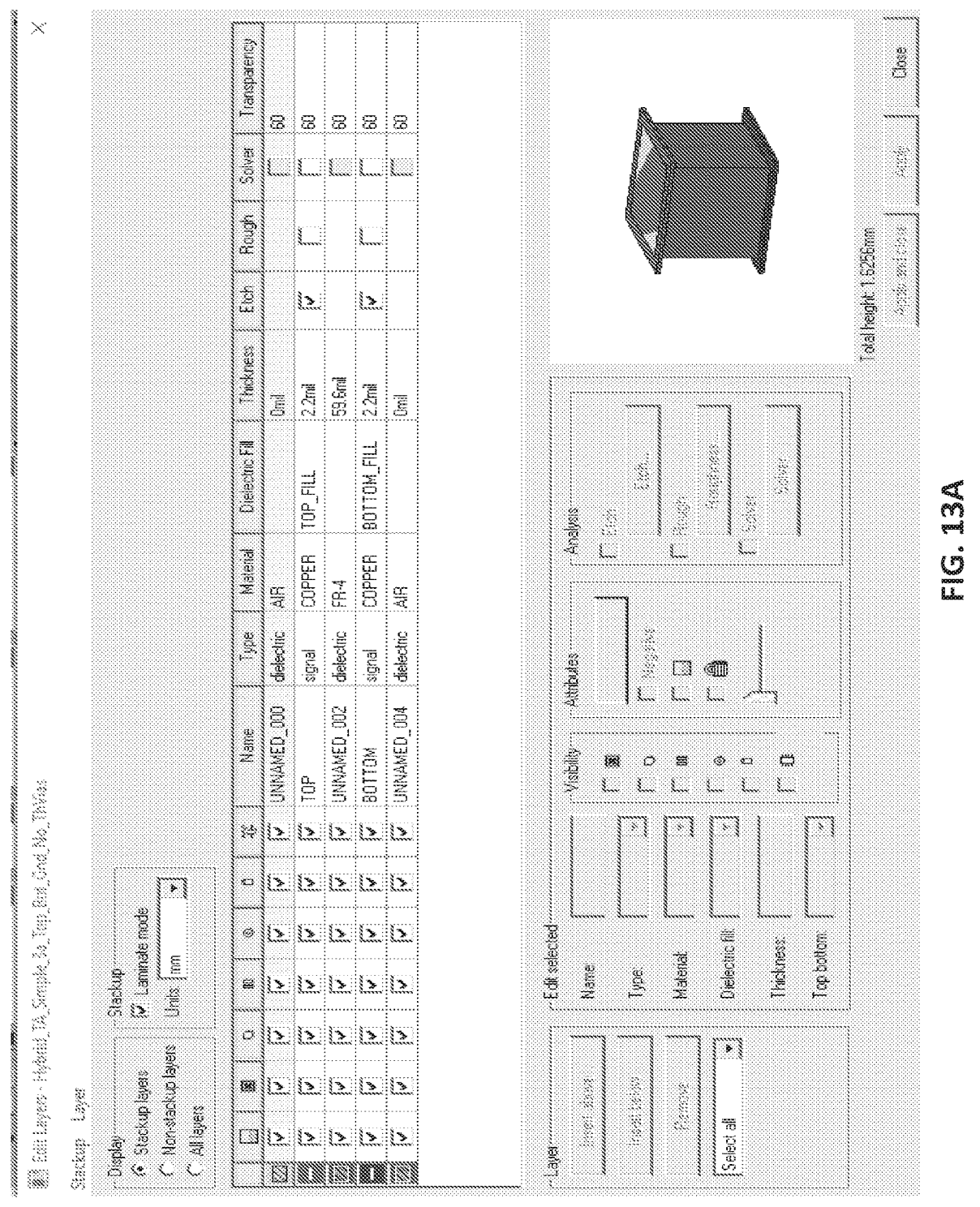
Figure 13B:
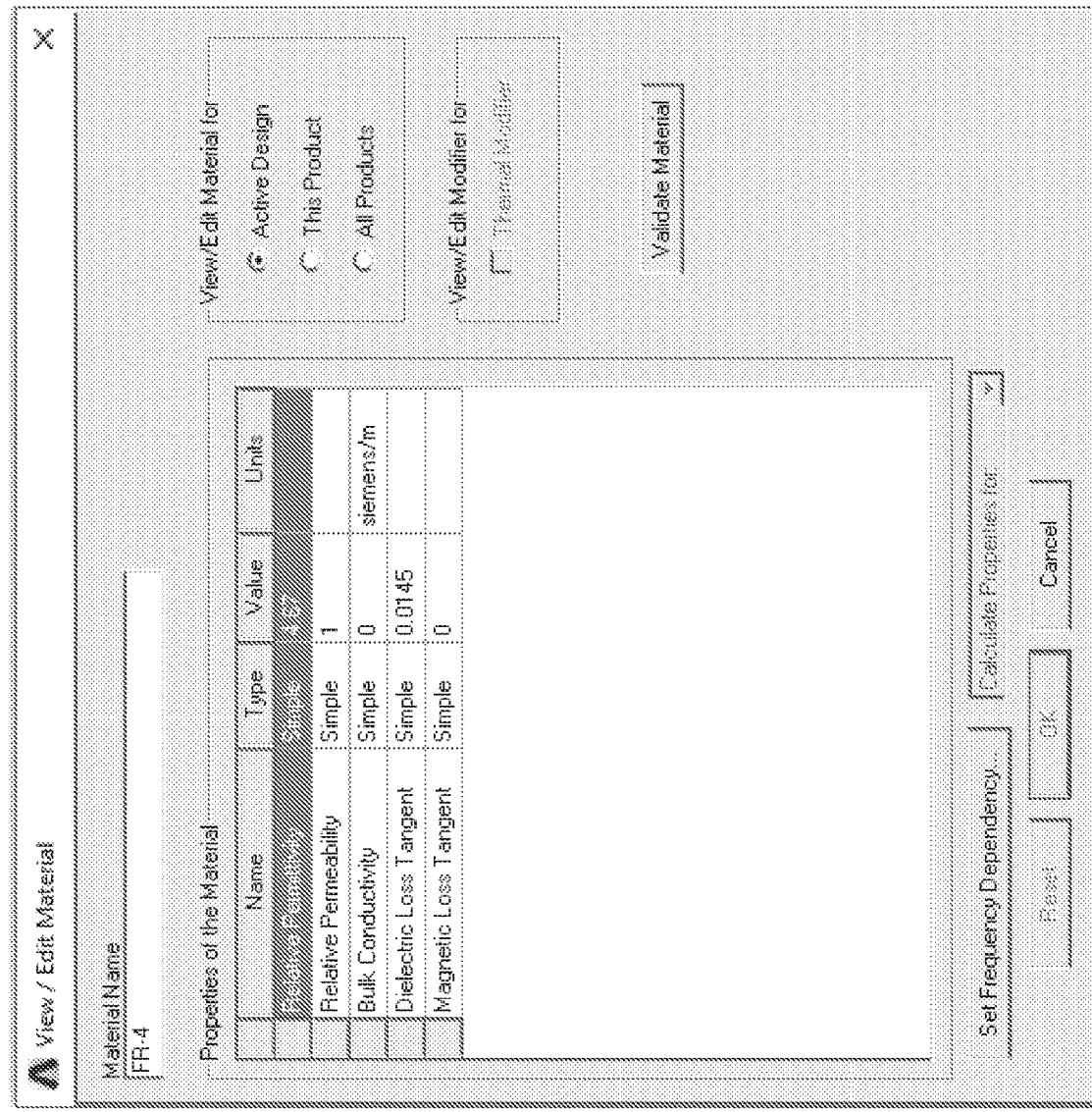
FIG. 13B illustrates an example of further simulation parameters of an applicator in a high-power pulsed electromagnetic field (PEMF) applicator system.

FIG. 12C illustrates an example of a circuit layout of an applicator in the high-power pulsed electromagnetic field (PEMF) applicator system in a simulation software. FIG. 13A illustrates an example of simulation parameters of the applicator in the high-power pulsed electromagnetic field (PEMF) applicator system in FIG. 12C. For example, the applicator has a 62 mil layer thickness board. FIG. 13B illustrates an example of further simulation parameters of the applicator in the high-power pulsed electromagnetic field (PEMF) applicator system in FIG. 12C.

Figure 14:
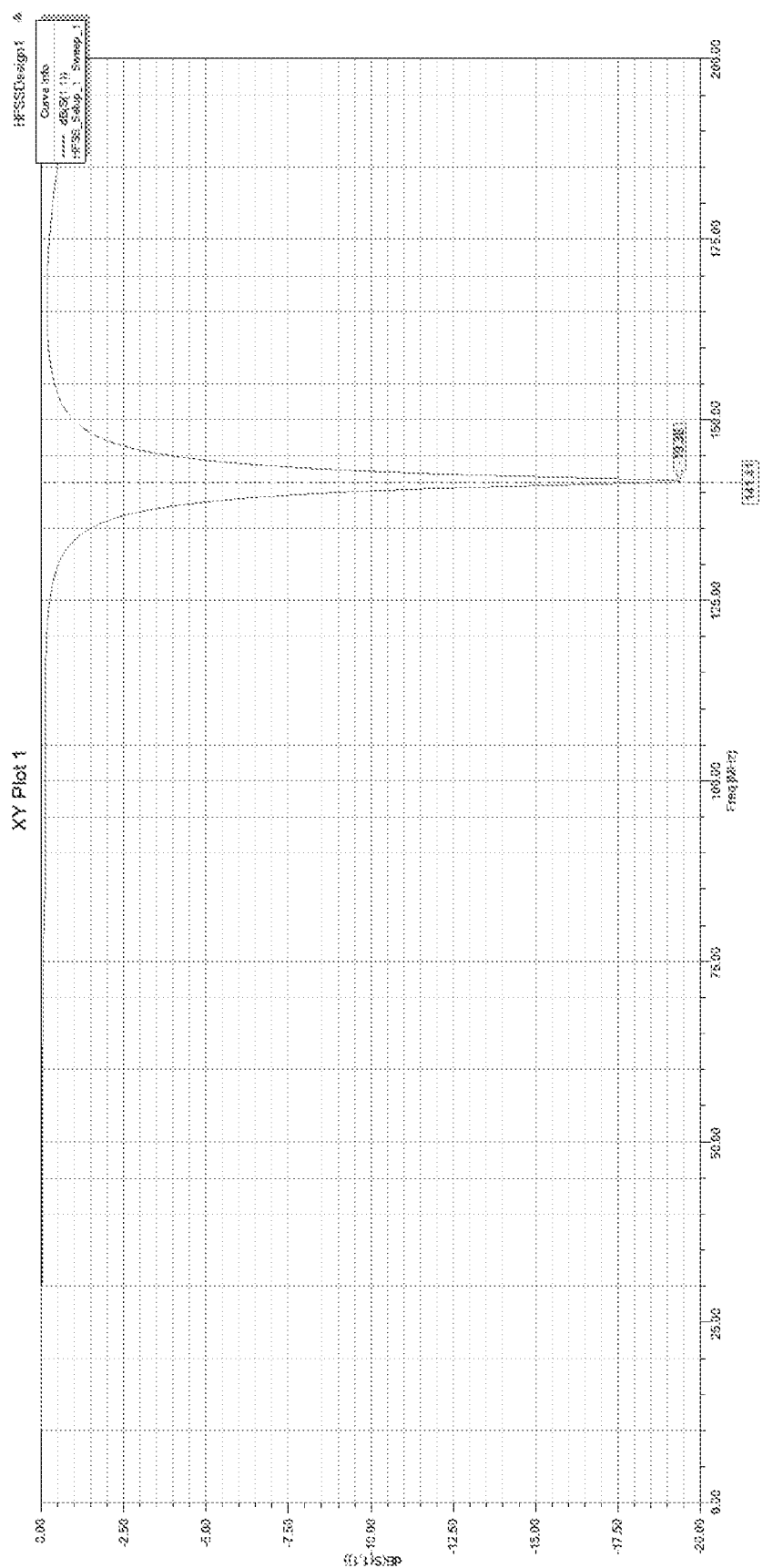
FIG. 14 illustrates an example of simulation results of an applicator of a high-power pulsed electromagnetic field (PEMF) applicator system.

FIG. 14 illustrates an example of simulation results of the applicator in the high-power pulsed electromagnetic field (PEMF) applicator system in FIG. 12C. The peak shows frequency of the coil circuit. In this example, the frequency is 141 MHz, which is terribly mismatched for 27 MHz signal. After the signals go through the matching circuits, the signals match to the antenna, which include both frequency response matching in addition to impedance matching.

Figure 15:
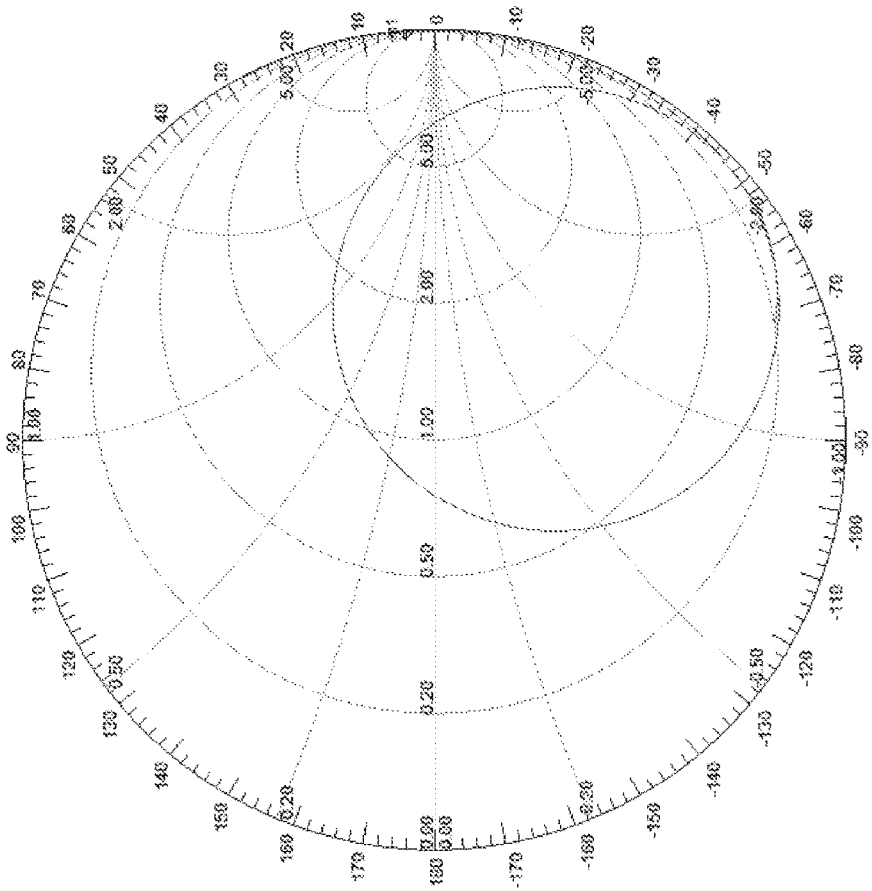
FIG. 15 illustrates an example of further results of an applicator in a high-power pulsed electromagnetic field (PEMF) applicator system.

FIG. 15 illustrates an example of further results of the applicator in the high-power pulsed electromagnetic field (PEMF) applicator system in FIG. 12C. Measure of impedance before it gets converted to 50 Ohms is shown in FIG. 15.

Figure 16:
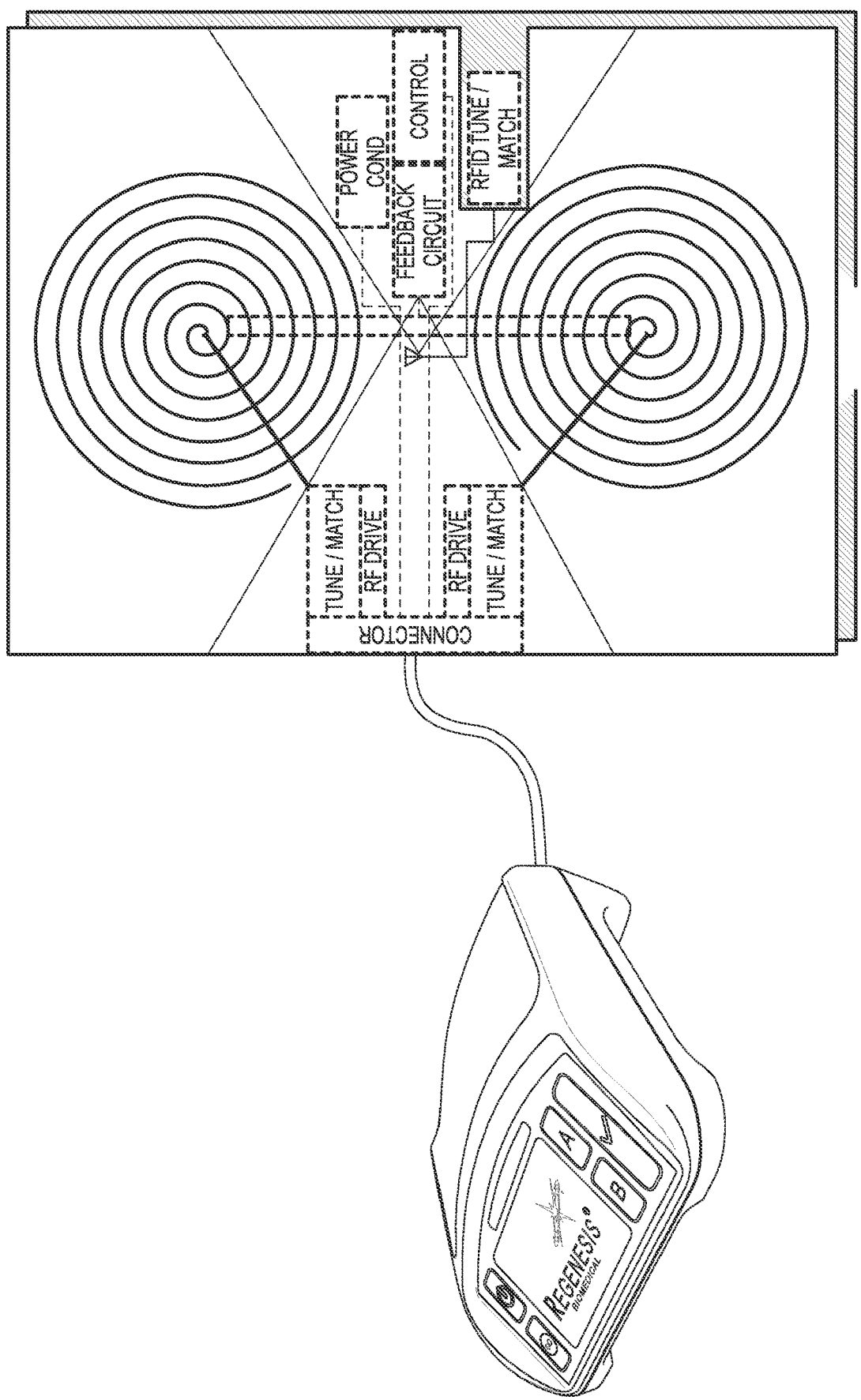
FIG. 16 schematically illustrates one example of dual applicator of a high-power pulsed electromagnetic field (PEMF) applicator system.

FIG. 16 schematically illustrates one example of dual coil circuits of a high-power pulsed electromagnetic field (PEMF) applicator system, where each of the one or more applicators comprises two generator, two coil circuits and two sets of matching networks.

As shown in FIG. 16, the layout of the applicator board comprises two coils, and the applicator is connected to the housing by a single cable. The control/addressing is configured to have two address decoders. The applicator can include a single feedback circuit. A single feedback detection can be sent back to detector and the controller in the base housing. A single 27 MHz carrier frequency can be switched to two different coils.

It is advantageous to have dual coil in a single applicator. For example, if the patient wants to treat feet, the patient would need two different treatment cycles for both feet, which can be inconvenient. With this dual coils applicator, the treatment time can be decreased by half. In addition, the dual coils applicator can be used to treat a larger area than a single coil applicator.

In general, described here is a high-power pulsed electromagnetic field (PEMF) applicator. The applicator can include a drive circuitry configured to receive a low-power control signal from a controller, wherein the drive circuitry comprises a generator configured to generate high-power pulsed electromagnetic field signal having a power of 40 W or greater based on the low-power control signal. The applicator can include a coil circuit configured to apply the high-power pulsed electromagnetic field signal to a subject, an electromagnetic energy shield disposed over the drive circuitry, and a detector configured to detect a field strength of the high-power pulsed electromagnetic field signal applied by the coil circuit, wherein the detector is configured to transmit the field strength to the controller so that the controller can adjust the low-power control signal in response to the detected field strength.

For example, the detector is disposed on an opposite side of a printed circuit board from the coil circuit to prevent capacitive coupling. For example, the generator is configured to generate pulsed radio frequency (RF) electromagnetic energy having a carrier frequency of 27 MHz. For example, the drive circuitry further comprises one or more impedance matching circuits.

For example, the applicator can further include an address decoder. For example, the applicator can further include a shield board configured to allow the electromagnetic energy to emit primarily in one direction. For example, the applicator can further include an antenna board.

Also described herein are methods for treating a patient with high-power pulsed electromagnetic fields. The methods can include providing a low-power control signal including a gating code from a controller in a base housing, transmitting the low-power control signal to at least one hand-held applicator in communication with the base housing, generating, in the hand-held applicator, a high-power, pulsed electromagnetic field signal based on the low-power control signal when the gating code matches an identifier code for the hand-held applicator, emitting the high-power, pulsed electromagnetic field signal from a coil in the at least one applicator, and detecting the emitted high-power, pulsed electromagnetic field signal using a detector that is coupled to an opposite side of the coil in the hand-held applicator.

For example, the methods can further include the step of transmitting the control signal having 15 V or lower. For example, the methods can further include the step of adjusting the low-power control signal based on the detected emitted high-power, pulsed electromagnetic field signal. For example, the methods can further include the step of running diagnosis and generating an error code in the base housing.

For example, the methods can further include the step of transmitting the low-power control signal to a plurality of hand-held applicators. For example, the methods can further include the step of wirelessly receiving, in the base housing, instructions from a remote server.

For example, the methods can further include the step of transmitting a radio frequency identification (RFID) address between the hand-held applicator and the base housing and, further wherein the hand-held applicator may generate the high-power, pulsed electromagnetic field only after the base housing verifies the RFID address.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A high-power pulsed electromagnetic field (PEMF) applicator system, the system comprising:
   a base housing comprising a controller configured to generate a low-power control signal; and
   one or more applicators coupled to the base housing, each applicator comprising:
   a drive circuitry comprising a generator configured to receive the low-power control signal and to produce, in the applicator, a high-power, pulsed electromagnetic field signal based on the low-power control signal, wherein the high-power pulsed electromagnetic field signal has a power of greater than 40 W;
   a coil circuit configured to emit the high-power pulsed electromagnetic field signal;
   a feedback circuit positioned behind the coil circuit and configured to detect a field strength of the high-power pulsed electromagnetic field signal emitted by the coil circuit and reject capacitively coupled PEMF interference signals from the coil circuit;
   an electromagnetic energy shield disposed between the drive circuitry and the coil circuit; and
   wherein the feedback circuit is disposed on an opposite side of a printed circuit board with respect to the coil circuit to limit capacitive coupling.

2. The system of claim 1, wherein the one or more applicators comprises two or more applicators.

3. The system of claim 1, wherein the controller is configured to adjust an amplitude of the high-power pulsed electromagnetic field in response to the detected field strength by adjusting the low-power control signal.

4. The system of claim 1, wherein the high-power pulsed electromagnetic field signal has a carrier frequency of about 27.12 MHz.

5. The system of claim 1, wherein the controller comprises an energetic firmware configured to generate the low-power control signal.

6. The system of claim 1, wherein the controller further comprises a diagnostic unit configured to run diagnosis and generate an error code.

7. The system of claim 1, wherein the controller is wirelessly coupled to the one or more applicators.

8. The system of claim 1, wherein at least one applicator of the one or more applicators further comprises a shield board configured to shield one side of the coil circuit.

9. A high-power pulsed electromagnetic field (PEMF) applicator comprising:
   a drive circuitry configured to receive a low-power control signal from a controller, wherein the drive circuity comprises a generator configured to generate high-power pulsed electromagnetic field signal having a power of 40 W or greater based on the low-power control signal;
   a coil circuit configured to apply the high-power pulsed electromagnetic field signal to a subject;
   an electromagnetic energy shield disposed over the drive circuitry; and
   a detector configured to detect a field strength of the high-power pulsed electromagnetic field signal applied by the coil circuit,
   wherein the detector is positioned behind the coil circuit and configured to transmit the field strength to the controller;
   wherein the controller is configured to adjust the low-power control signal in response to the detected field strength;
   wherein the detector is further configured to reject capacitively coupled PEMF interference signals from the coil circuit; and
   wherein the detector is disposed on an opposite side of a printed circuit board with respect to the coil circuit to limit capacitive coupling.

10. The applicator of claim 9, wherein the generator is configured to generate pulsed radio frequency (RF) electromagnetic energy having a carrier frequency of 27.12 MHz.

11. The applicator of claim 9, further comprising an address decoder.

12. The applicator of claim 9, further comprising a shield board configured to allow the electromagnetic energy to emit primarily in one direction.

13. The applicator of claim 9, further comprising an antenna board.

14. A method for treating a patient with high-power pulsed electromagnetic fields (PEMF), the method comprising:
   providing a low-power control signal including a gating code from a controller in a base housing;
   transmitting the low-power control signal to at least one hand-held applicator in communication with the base housing;
   generating, in the hand-held applicator, a high-power, pulsed electromagnetic field signal dependent on the low-power control signal based on the gating code matching an identifier code for the hand-held applicator, wherein the high-power pulsed electromagnetic field signal has a power of greater than 40 W;
   emitting the high-power, pulsed electromagnetic field signal from a coil in the at least one applicator;
   detecting the emitted high-power, pulsed electromagnetic field signal using a detector that is coupled to an opposite side of the coil in the hand-held applicator;
   wherein the detector is disposed on an opposite side of a printed circuit board with respect to the coil circuit to limit capacitive coupling; and wherein the detector is configured to reject capacitively coupled PEMF interference signals from the coil.

15. The method of claim 14, further comprising adjusting the low-power control signal based on the detected emitted high-power, pulsed electromagnetic field signal.

16. The method of claim 14, further comprising running diagnosis and generating an error code in the base housing.

17. The method of claim 14, wherein transmitting comprises transmitting the low-power control signal to a plurality of hand-held applicators.

18. The method of claim 14, further comprising wirelessly receiving, in the base housing, instructions from a remote server.

\* \* \* \* \*